(12) United States Patent
Makwana

(10) Patent No.: US 11,478,360 B2
(45) Date of Patent: *Oct. 25, 2022

(54) MOTION PRESERVING SPINAL IMPLANT FOR TOTAL DISC REPLACEMENT

(71) Applicant: Nayan Manharlal Makwana, Naples, FL (US)

(72) Inventor: Nayan Manharlal Makwana, Naples, FL (US)

(73) Assignee: SPINVENTION, LLC, Naples, FL (US)

( * ) Notice: Subject to any disclaimer, the term of this patent is extended or adjusted under 35 U.S.C. 154(b) by 233 days.

This patent is subject to a terminal disclaimer.

(21) Appl. No.: 16/940,234

(22) Filed: Jul. 27, 2020

(65) Prior Publication Data

US 2020/0352733 A1    Nov. 12, 2020

Related U.S. Application Data

(63) Continuation-in-part of application No. 16/826,742, filed on Mar. 23, 2020, now Pat. No. 10,758,362, which is a continuation-in-part of application No. 29/687,050, filed on Apr. 10, 2019, now Pat. No. Des. 900,318.

(60) Provisional application No. 62/828,584, filed on Apr. 3, 2019, provisional application No. 62/837,474, filed on Apr. 23, 2019.

(51) Int. Cl.
*A61F 2/44* (2006.01)
*A61F 2/30* (2006.01)

(52) U.S. Cl.
CPC .. *A61F 2/4425* (2013.01); *A61F 2002/30069* (2013.01); *A61F 2002/30112* (2013.01); *A61F 2002/30387* (2013.01); *A61F 2002/30448* (2013.01); *A61F 2002/30899* (2013.01); *A61F 2002/443* (2013.01); *A61F 2310/00005* (2013.01)

(58) Field of Classification Search
CPC .............. A61F 2/4425; A61F 2002/443; A61F 2002/30069; A61F 2002/30227
See application file for complete search history.

(56) References Cited

U.S. PATENT DOCUMENTS

| 7,799,083 B2 | 9/2010 | Smith et al. |
| 8,172,904 B2 | 5/2012 | Duggal et al. |
| 8,613,768 B2 | 12/2013 | Biedermann et al. |

(Continued)

*Primary Examiner* — Christian A Sevilla

(57) ABSTRACT

A motion preserving spinal implant is presented for use in placement between intervertebral space for total replacement of a degenerated spinal disc. The motion preserving spinal implant has a pair of end plates sandwiched around an inner core and an outer core, with the inner core being concentrically positioned within the outer core. The outer core encapsulates the inner core and provides adequate sealing of the inner core while maintaining flexibility and elasticity to advantageously support physiological movements. The inner core is constructed of an elastomeric material and acts as a solid diaphragm in order to resist and withstand localized compression and other forces. The end plates provide anchoring and fusion with adjoining vertebra and hold the inner and outer cores in place. The motion preserving spinal implant restores the normal height and natural function of the degenerated spinal disc and preserves the natural motion of the spine.

18 Claims, 24 Drawing Sheets

(56) References Cited

U.S. PATENT DOCUMENTS

| | | | |
|---|---|---|---|
| 9,220,603 B2 | 12/2015 | Arramon | |
| 10,758,362 B1* | 9/2020 | Makwana | A61F 2/4425 |
| 2002/0035400 A1* | 3/2002 | Bryan | A61F 2/4425 |
| | | | 623/17.15 |
| 2004/0030391 A1* | 2/2004 | Ferree | A61F 2/38 |
| | | | 623/17.15 |
| 2004/0068320 A1* | 4/2004 | Robie | A61F 2/4425 |
| | | | 623/23.6 |
| 2005/0020768 A1* | 1/2005 | Pause | D06N 3/128 |
| | | | 524/860 |
| 2005/0165486 A1* | 7/2005 | Trieu | A61F 2/442 |
| | | | 623/17.13 |
| 2006/0235524 A1* | 10/2006 | Petit | A61F 2/4425 |
| | | | 623/17.13 |
| 2013/0079811 A1* | 3/2013 | Agnew | A61B 17/0057 |
| | | | 606/213 |

* cited by examiner

SECTION H-H

MOTION PRESERVING SPINAL IMPLANT FOR TOTAL DISC REPLACEMENT

The current application is a continuation-in-part (CIP) application of a U.S. non-provisional application Ser. No. 16/826,742 filed on Mar. 23, 2020. The U.S. non-provisional application Ser. No. 16/826,742 claims a priority to the U.S. Provisional Patent application Ser. No. 62/828,584 filed on Apr. 3, 2019. The U.S. non-provisional application Ser. No. 16/826,742 also claims a priority to the U.S. Provisional Patent application Ser. No. 62/837,474 filed on Apr. 23, 2019.

FIELD OF THE INVENTION

The present invention relates generally to human body implants. More particularly, the present invention relates to a motion preserving spinal implant for replacement of a spinal disc.

BACKGROUND OF THE INVENTION

Spinal implants are intended to treat degenerative disc disease (DDD) or other disc injuries. Spinal fusion treatment is a widely used treatment to alleviate pain, but limits range of motion and mobility for a patient. Total disc replacement is another treatment for disc degenerative disease that aims to preserve motion and limit complications related to spinal fusion such as adjacent level wear and disc degeneration. Total disc replacement is an effective solution for degenerative disc disease and gaining interest due to increasing prevalence of neck pain, lower back pain, and pain in general. Thus, there is a need for functional improvement. For an example, without limitations, there is a need for total disc replacement spinal implants that reduce wear due to metal to metal sliding and corrosive surfaces, increase cushioning, improve shock absorption, reduce wear debris of metal, and maintain spinal motion range.

The present invention solves these problems by providing a treatment solution that reduces degeneration due to metal wear because of no sliding between metal plates, increases cushioning with effective inner core design features, and uses special polymeric and elastomeric materials having varying hardness and physical properties such as silicone or liquid silicon rubber that also provides shock absorption, and maintains range of motion due to effective outer core design, its features, and choice of materials. All components in the assembly are designed such that it can effectively resist compression forces, shear-compression forces, and torsion forces.

Additional advantages of the invention will be set forth in part in the description which follows, and in part will be obvious from the description, or may be learned by practice of the invention. Additional advantages of the invention may be realized and attained by means of the instrumentalities and combinations particularly pointed out in the detailed description of the invention section. Further benefits and advantages of the embodiments of the invention will become apparent from consideration of the following detailed description given with reference to the accompanying drawings, which specify and show preferred embodiments of the present invention.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

The present invention is a spinal implant intended for use in total replacement of a degenerated spinal disc. In general, referring to FIGS. 1-5, the present invention comprises a first end plate 1, a second end plate 2, an inner core 3, and an outer core 4. In some embodiments of the present invention, the first end plate 1, the second end plate 2, the inner core 3, and the outer core 4 each have generally radial geometry, though it may be noted that other geometries may be utilized as desired or useful. The inner core 3 and the outer core 4 are substantially wider than tall, having a certain thickness, or axial height. As previously mentioned, in some embodiments, the inner core 3 and the outer core 4 each have radial geometry and are generally disc shaped, having a radial axial cross section. In some embodiments, the first end plate 1, the second end plate 2, the inner core 3, and the outer core 4 may have other general geometries. For example, as shown in FIGS. 16-24, in some embodiments, the first end plate 1, the second end plate 2, the inner core 3, and the outer core 4 each have generally rectilinear peripheral geometry with rounded corners.

Figure 5:
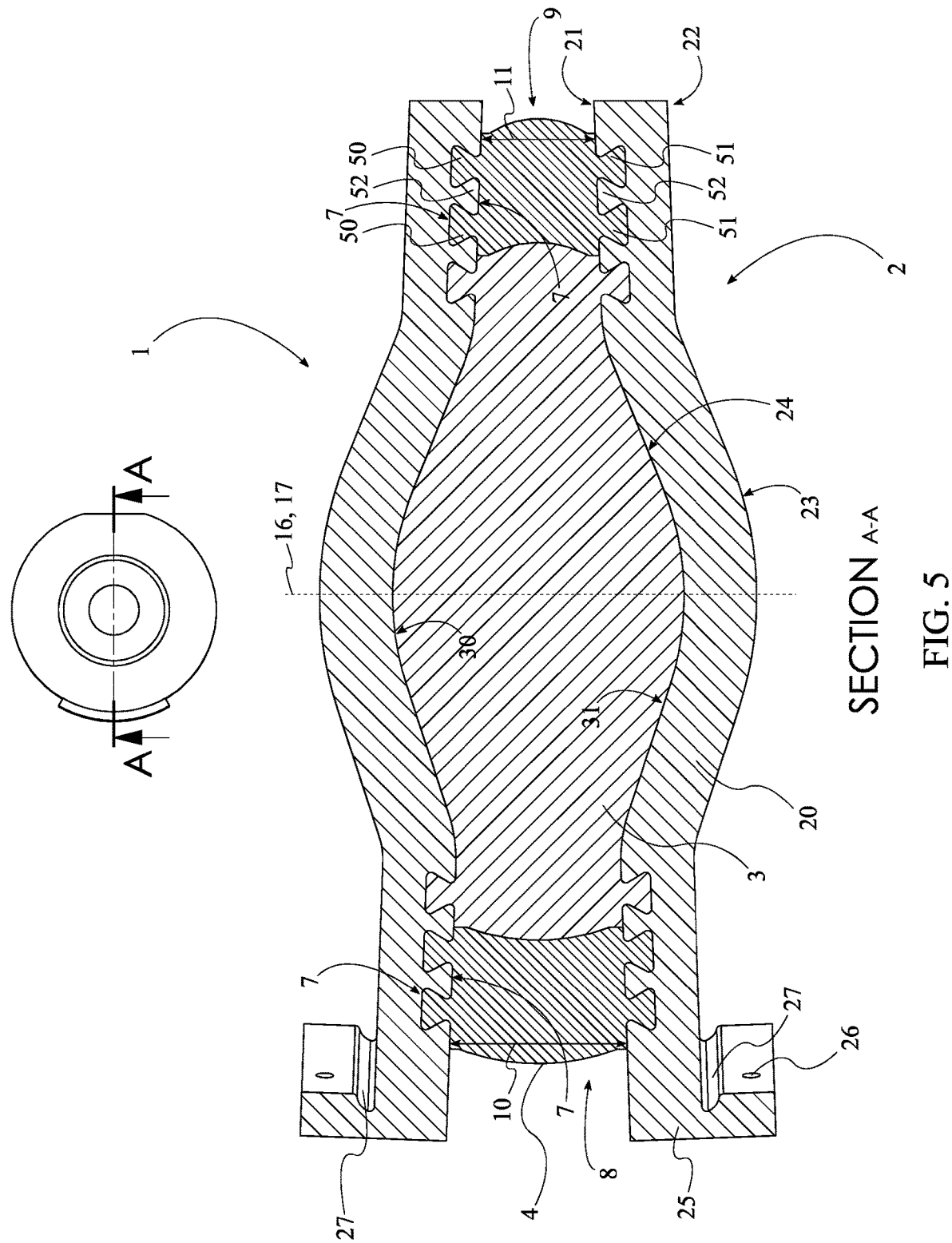
FIG. 5 is a top view and a side sectional view of the present invention.
Figure 6:
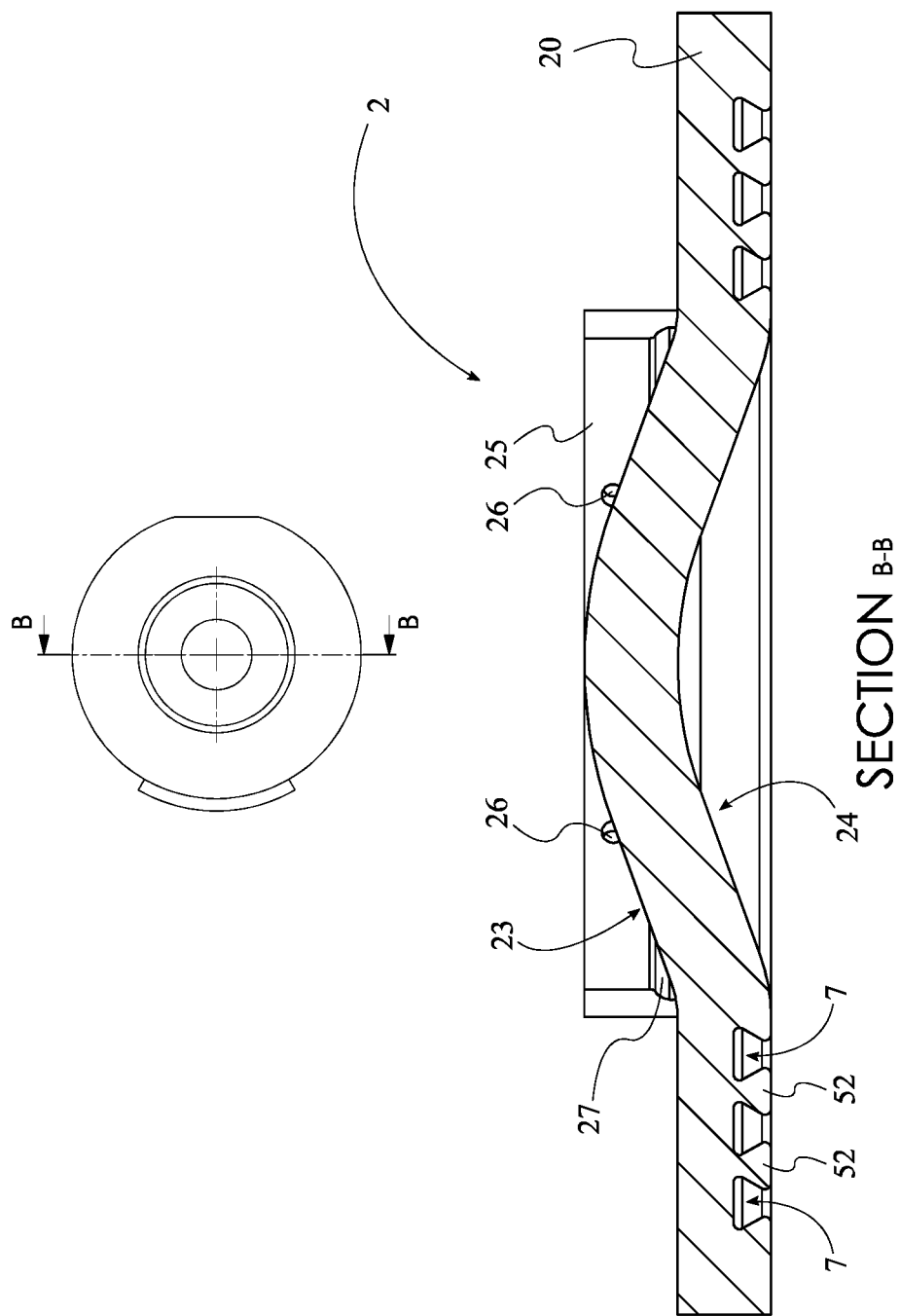
FIG. 6 is a top view and a front sectional view of one of the end plates of the present invention.

In the preferred embodiment, the inner core 3 is positioned within the outer core 4. In some embodiments, the inner core 3 is positioned concentrically within the outer core 4, wherein the inner core 3 comprises an inner core centerline 16 and the outer core 4 comprises an outer core centerline 17, as shown in FIGS. 2, 5, 7, 8, 12, 13, and 21. The inner core centerline 16 and the outer core centerline 17 are positioned coincident with each other in order for the inner core 3 and the outer core 4 to be positioned concentrically with each other, as illustrated in FIG. 5. In some embodiments, the inner core 3 and the outer core 4 may be positioned such that they are not exactly concentric with each other, and thus the inner core centerline 16 and the outer core centerline 17 are positioned offset from each other, either through translation or rotation, or both.

In the preferred embodiment, the outer core 4 comprises an inner cavity 40, and the inner cavity 40 centrally traverses through the outer core 4. Said central traversement is not intended to mean that the inner cavity 40 is necessarily concentric with the outer perimeter of the outer core 4, but rather that the inner cavity 40 traverses through the outer core 4 in a generally centralized position relative to the outer perimeter of the outer core 4. In some embodiments, however, the inner cavity 40 is positioned concentrically within the outer core 4, such that the inner cavity 40 centrally and axially traverses through the outer core 4. The inner core 3 is positioned within the inner cavity 40 of the outer core 4, wherein the inner core 3 is sealed by the outer core 4, the first end plate 1 and the second end plate 2. In some embodiments, the inner core 3 is positioned concentrically within the inner cavity 40. In some embodiments, the internal lateral geometry of the inner cavity 40 may be determined by the external lateral geometry of the outer core 4.

In various embodiments, the first end plate 1, second end plate 2, inner core 3, and outer core 4 may be positioned concentrically with each other, wherein each of the first end plate 1, second end plate 2, inner core 3, and outer core 4 comprise a centerline, wherein the centerlines of the first end plate 1, second end plate 2, inner core 3, and outer core 4 are aligned with each other when the first end plate 1, second end plate 2, inner core 3, and outer core 4 are positioned concentrically with each other. In other embodiments, one or more of the first end plate 1, second end plate 2, inner core 3, and outer core 4 may not be positioned concentrically with each other, wherein the centerlines of one or more of the said components may be positioned offset from each other, either through linear translation or rotation—an offset centerline may be positioned parallel to one or more other centerlines of the aforementioned components, but offset through a linear distance, or an offset centerline may be oriented at an angle offset to one or more other centerlines of the aforementioned components. In some embodiments, such a said centerline may also correspond to a radial axis, or axis of revolution, of the generally radial features of said components.

In the preferred embodiment, the outer core 4 is connected between the first end plate 1 and the second end plate 2. In some embodiments, as shown in FIGS. 1-11, the outer core 4 is connected between the first end plate 1 and the second end plate 2 through a plurality of interlocking members 5. In some embodiments, the outer core 4 is connected between the first end plate 1 and the second end plate 2 through an adhesive. FIGS. 12-15 and FIGS. 20-24 illustrate examples of such embodiments. The adhesive may be any suitable adhesive appropriate for the intended use of the present invention. The adhesive should be sterile, biodegradable and biocompatible. The adhesive may be based on, derived from, or comprise, but is not limited to, bone cement, polyurethane, acrylates, rubbers, polymers, epoxy resins, phenolic resins, natural adhesives, synthetic adhesives, or any other suitable adhesive substances. Alternatively, the adhesive may be the result of any suitable manufacturing process, as opposed to a distinct adhesive substance.

Thus, the inner core 3 and the outer core 4 are sandwiched by the first end plate 1 and the second end plate 2. More specifically, as previously mentioned, the outer core 4 comprises the inner cavity 40 that centrally and traverses through the outer core 4, with the inner core 3 being positioned within the inner cavity 40 of the outer core 4, such that the inner core 3 is sealed by the outer core 4, the first end plate 1 and the second end plate 2.

In the preferred embodiment, the inner core 3 is constructed of a polymeric material. More particularly, in various embodiments, the inner core 3 is preferably constructed of a medical or implant grade polymeric or elastomeric material which may have varying hardness and other physical properties in various embodiments. In some embodiments, the inner core 3 is constructed of a liquid silicon rubber material, wherein the liquid silicon rubber material may have varying hardness properties in different embodiments. In some embodiments, the inner core 3 is constructed of a medical or implant grade silicone elastomer with a hardness ranging from 60 shore A to 90 shore A. In some embodiments, the inner core 3 may be constructed of a liquid silicone rubber (LSR) material. Such material is inert and widely used in medical breast implants. Silicone rubber has the ability to retain its initial shape and mechanical stress under high compression, shear-compression, flexural, torsional, and tensile stresses and has excellent creep properties. In other embodiments, other appropriate materials may be used to manufacture the inner core 3. The inner core 3 serves as a solid "diaphragm" or cushion that resists and withstands localized compression, shear-compression, torsion, and other forces. In various embodiments, the diameter of the inner core 3 may range from approximately 0.125 inches to 2.25 inches, but it should be understood herein that various dimensions of the present invention may vary without departing from the intended spirit and scope of the present invention.

Figure 7:
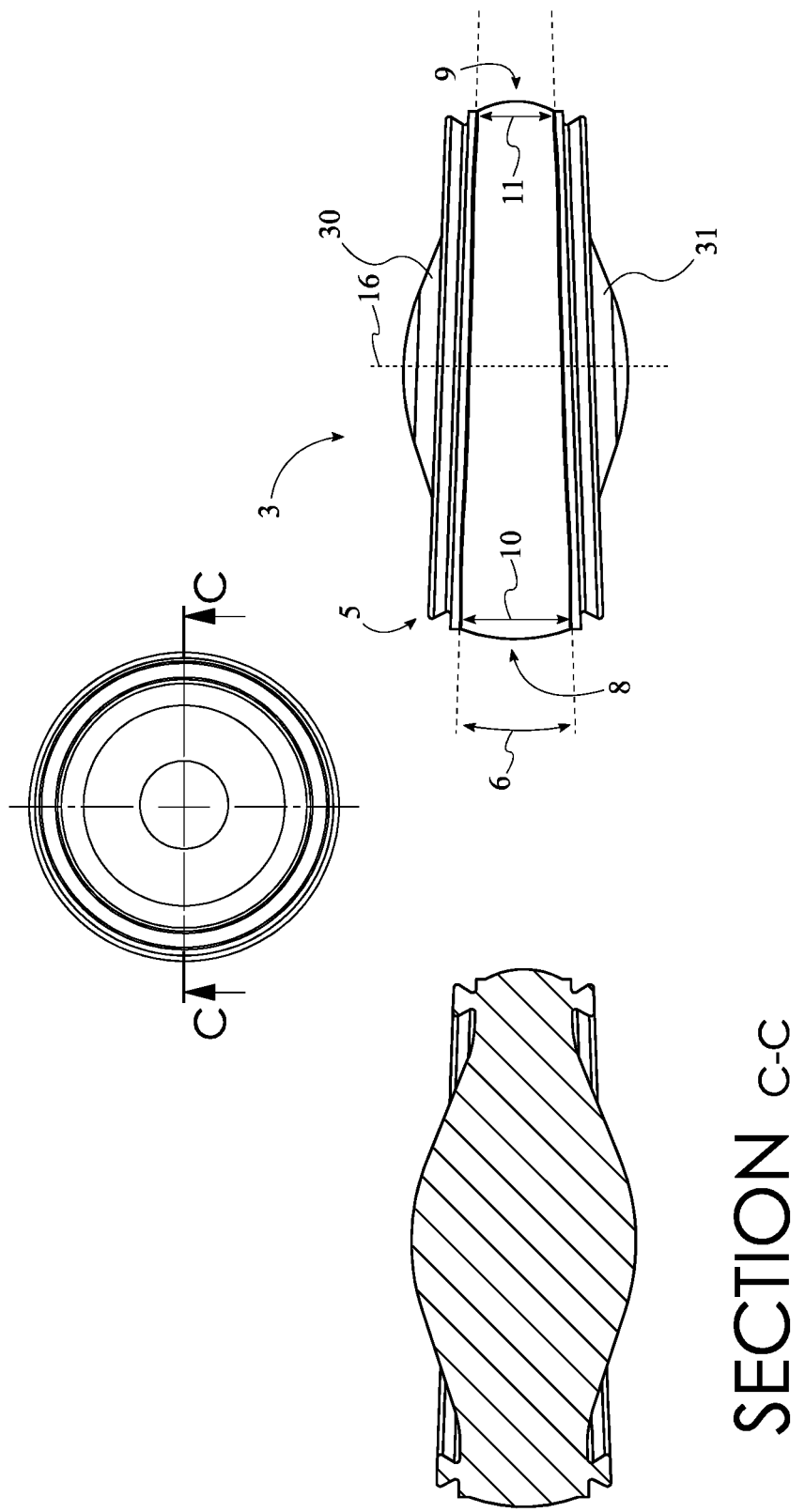
FIG. 7 is a top view, a side sectional view, and a side view of the inner core of the present invention.

In the preferred embodiment, the inner core 3 comprises a first core convexity 30 and a second core convexity 31, as shown in FIGS. 5 and 7. The first core convexity 30 and the second core convexity 31 are positioned opposite each other along a thickness of the inner core 3, along the inner core centerline 16. In some embodiments, the first core convexity 30 and the second core convexity 31 are positioned axially opposite each other along the thickness of the inner core 3, wherein the first core convexity 30 and the second core convexity 31 are concentrically positioned with the inner core centerline 16. In other embodiments, the first core convexity 30 and the second core convexity 31 may be positioned offset from the inner core centerline 16.

The first core convexity 30 and the second core convexity 31 are essentially bulges centrally positioned on the inner core 3 that contribute to the inner core's 3 capabilities to resist and withstand any forces the inner core 3 is subject to while installed in a human spine. The first core convexity 30 and the second core convexity 31 further correspond to and mate with inner concavities on the first end plate 1 and the second end plate 2, as will be discussed hereinafter. In various embodiments, a convexity angle of the first core convexity 30 and the second core convexity 31 may range from 5 degrees to 60 degrees, and an outer radius of the first core convexity 30 and the second core convexity 31 may range from 0.075 inches to 2 inches in various embodiments. In some embodiments, the inner core 3 further comprises a lateral wall with a convex curvature, whose radius may range in various embodiments from 0.063 inches to 2.250 inches, but it should be understood herein that various dimensions of the present invention may vary without departing from the intended spirit and scope of the present invention.

As previously mentioned, in some embodiments, the inner core 3 comprises an inner core centerline 16 and the outer core 4 comprises an outer core centerline 17. The inner core centerline 16 and the outer core centerline 17 may be considered in some embodiments to be an axis equidistant from the outer perimeter of the inner core 3 and outer core 4, respectively, and/or an axis of revolution for other radial features in some embodiments. Additionally or alternatively, in some embodiments, a radial axis may be considered as said axis of revolution, and may be considered as distinct from the inner core centerline 16 and the outer core centerline 17 for the inner core 3 and outer core 4, respectively. In various embodiments the radial axis may be positioned offset from the inner core centerline 16 and the outer core centerline 17. In such embodiments, the first core convexity 30 and the second core convexity 31 of the inner core 3 are concentrically positioned about the radial axis of the inner core 3. Furthermore, the inner cavity 40 of the outer core 4 is positioned concentrically about the radial axis of the outer core 4 in such embodiments.

The outer core 4 acts as a sealing ring for the inner core 3 and provides the necessary motion to the spine once the present invention is implanted in a human body. In the preferred embodiment, the outer core 4 is constructed of a polymeric or elastomeric material with varying hardness and other physical properties in various embodiments.

In various embodiments, the outer core 4 may be constructed of various materials. In the preferred embodiment, the outer core is constructed of a polymeric material. In some embodiments, the outer core is constructed of a liquid silicon rubber material, wherein the liquid silicon rubber material may have varying hardness properties in different embodiments. In some embodiments, the outer core 4 may be constructed of an ultra-high molecular weight polyethylene (UHMWPE) material. In some embodiments, the outer core 4 may be constructed of a medical grade polypropylene (PP) material, though the material of the outer core 4 may vary in different embodiments as desired. In general, it is desired to use a material with superior abrasive and corrosive resistance, high strength, light weight, and low coefficient of friction in the outer core 4. In various embodiments, the diameter of the outer core 4 may range from 0.175 inches to 2.375 inches, though as previously mentioned, any dimensions listed for the various components of the present invention should not be considered to be limiting and may vary in different embodiments.

In the preferred embodiment, the first end plate 1 and the second end plate 2 are each constructed of a polyether ether ketone (PEEK) material, though the material of the first end plate 1 and the second end plate 2 may vary in different embodiments. PEEK is increasingly employed as a biomaterial for trauma treatments, orthopedic, and spinal implants. It is inherently strong, inert, and biocompatible. Properties that make PEEK a material of choice for the end plates include: modulus similar to bone, reduced stress shielding, artifact-free imaging, and an osteoconductive surface for bone on-growth. Alternatively or additionally, PEEK material can be used in combination with a titanium material or with a titanium plasma spray on the external surfaces of the outer core 4. The first end plate 1 and the second end plate 2 may be externally treated with a titanium material in order to promote strength, abrasion resistance, and friction reduction.

In the preferred embodiment, as shown in FIGS. 1-6, the first end plate 1 and the second end plate 2 each comprise a plate body 20, an inner side 21, an outer side 22, a plate convexity 23, and a concavity 24, wherein a thickness of the plate body 20 extends between the inner side 21 and the outer side 22. In various embodiments, the diameter of the plate body 20 may range from 0.375 inches to 2.5 inches, while the thickness may range from 0.031 inches to 0.375 inches, but it should be understood herein that various dimensions of the present invention may vary without departing from the intended spirit and scope of the present invention.

Figure 1:
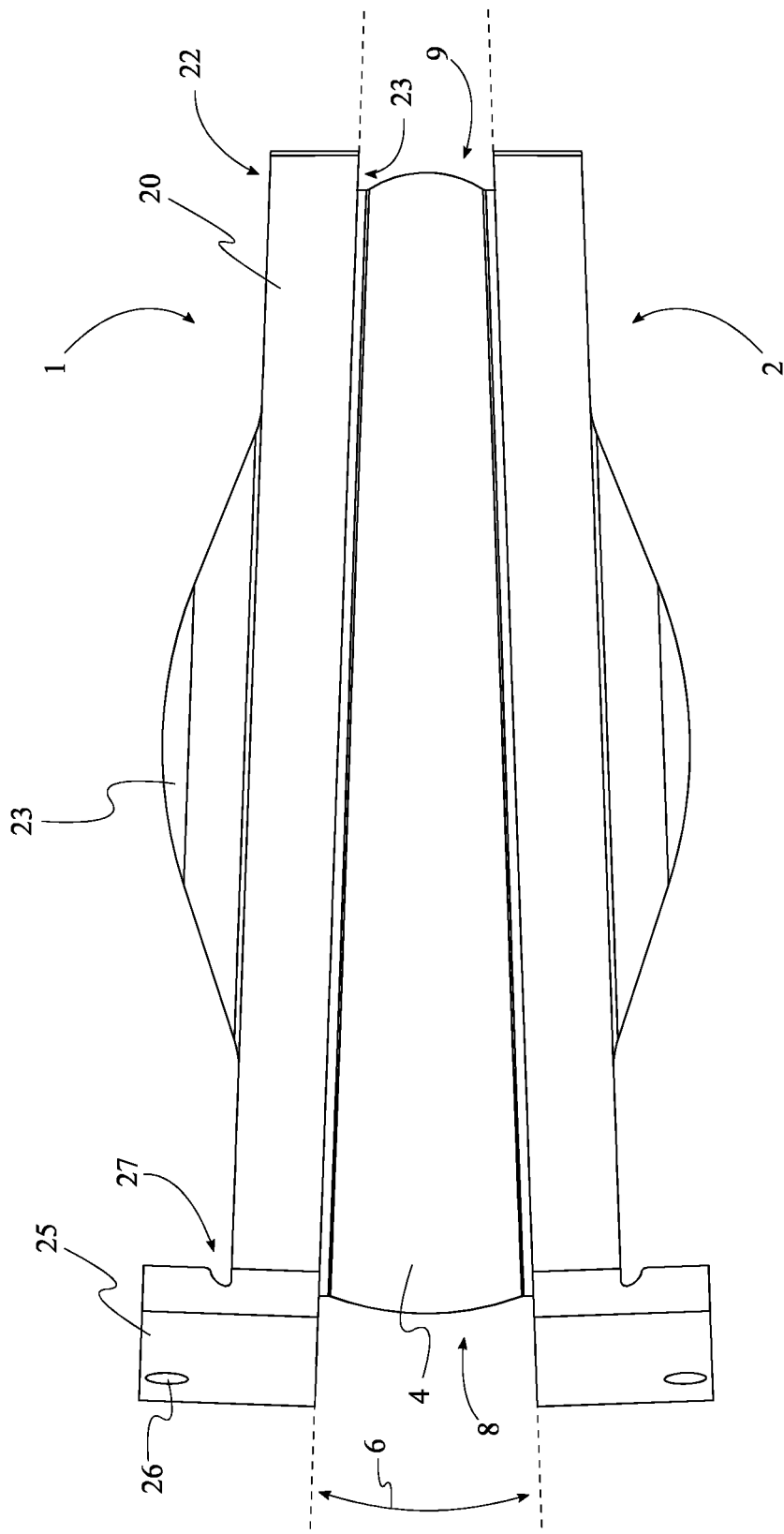
FIG. 1 is a side view of the present invention.
Figure 2:
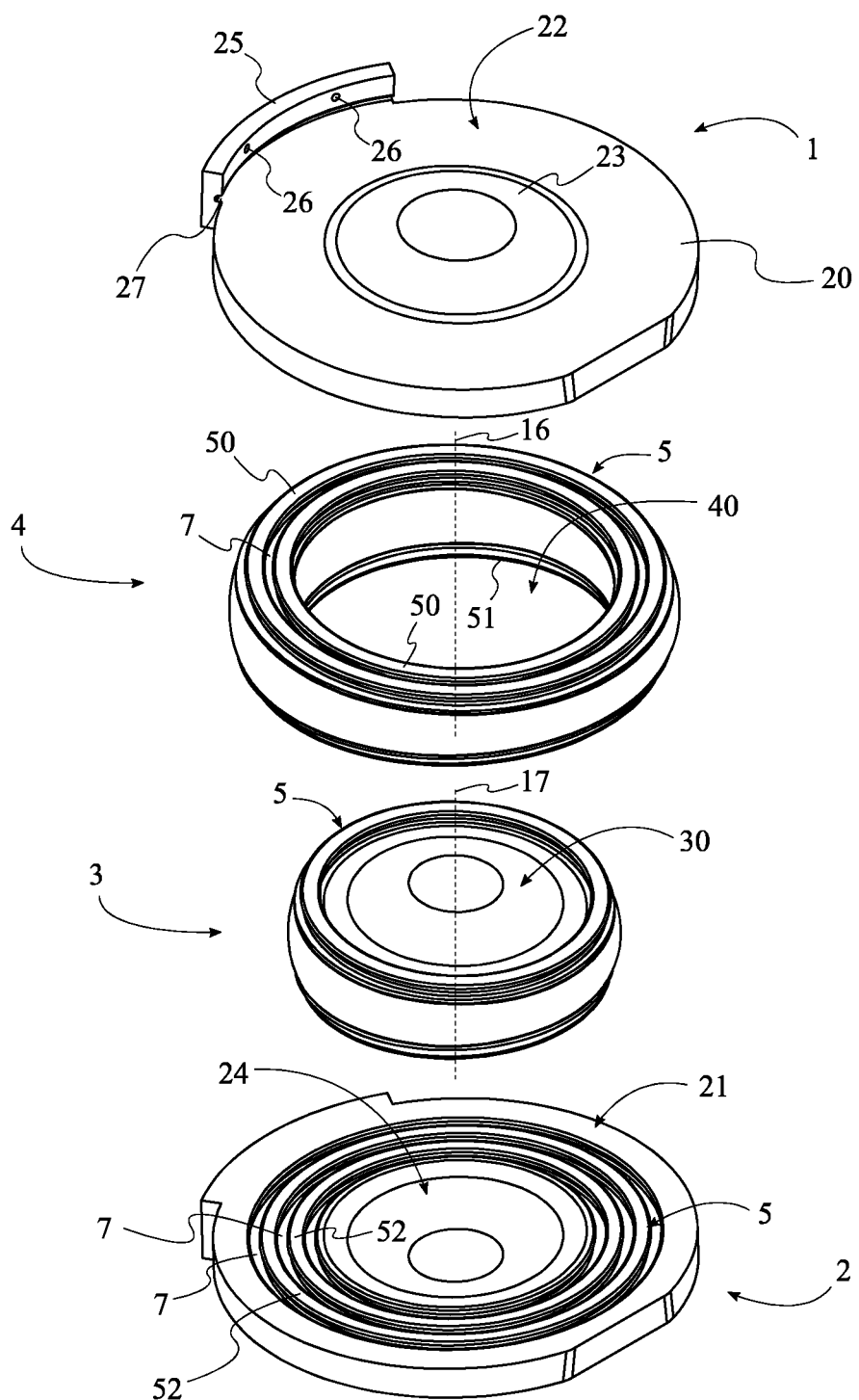
FIG. 2 is an exploded perspective view of the present invention.
Figure 3:
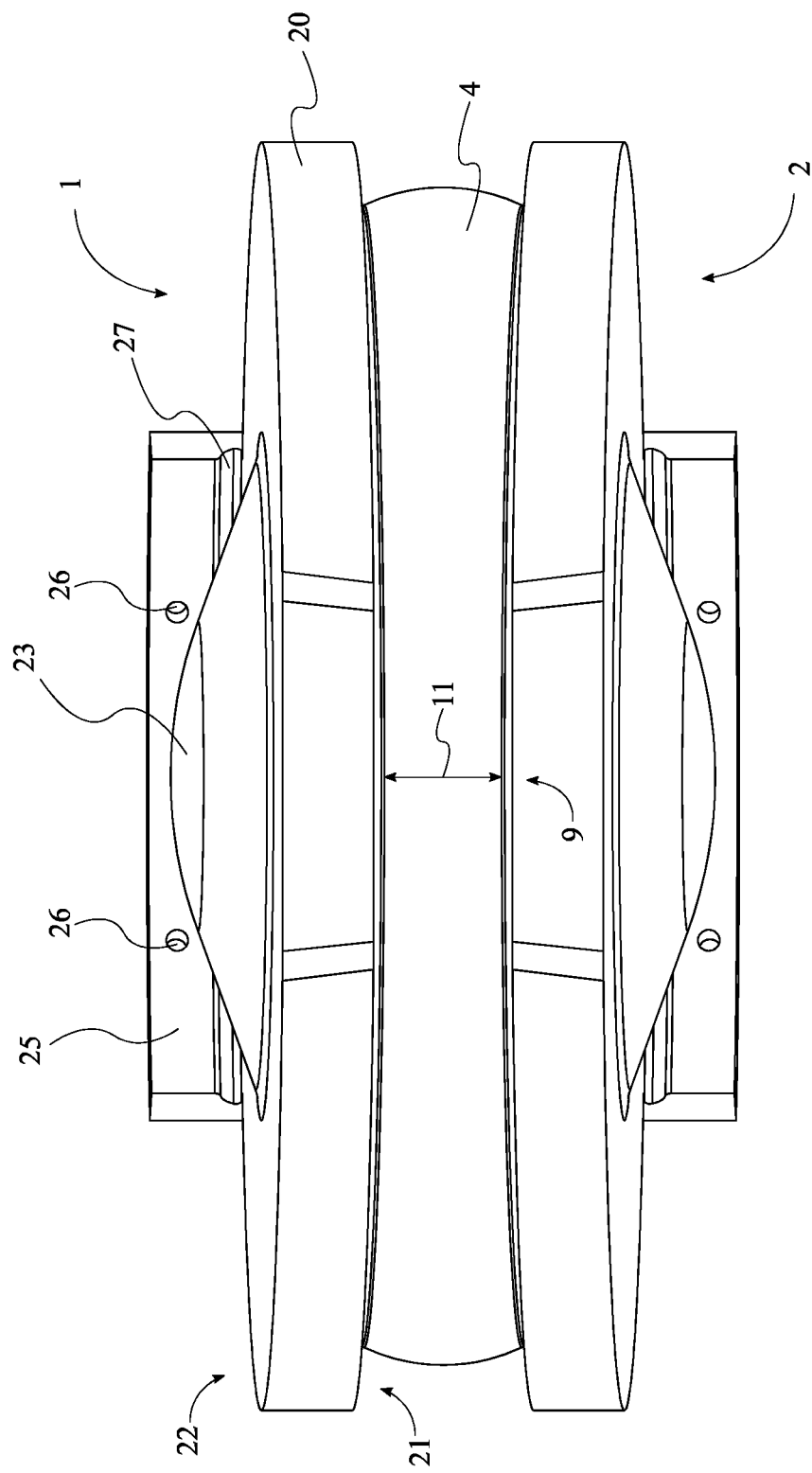
FIG. 3 is a front view of the present invention.
Figure 4:
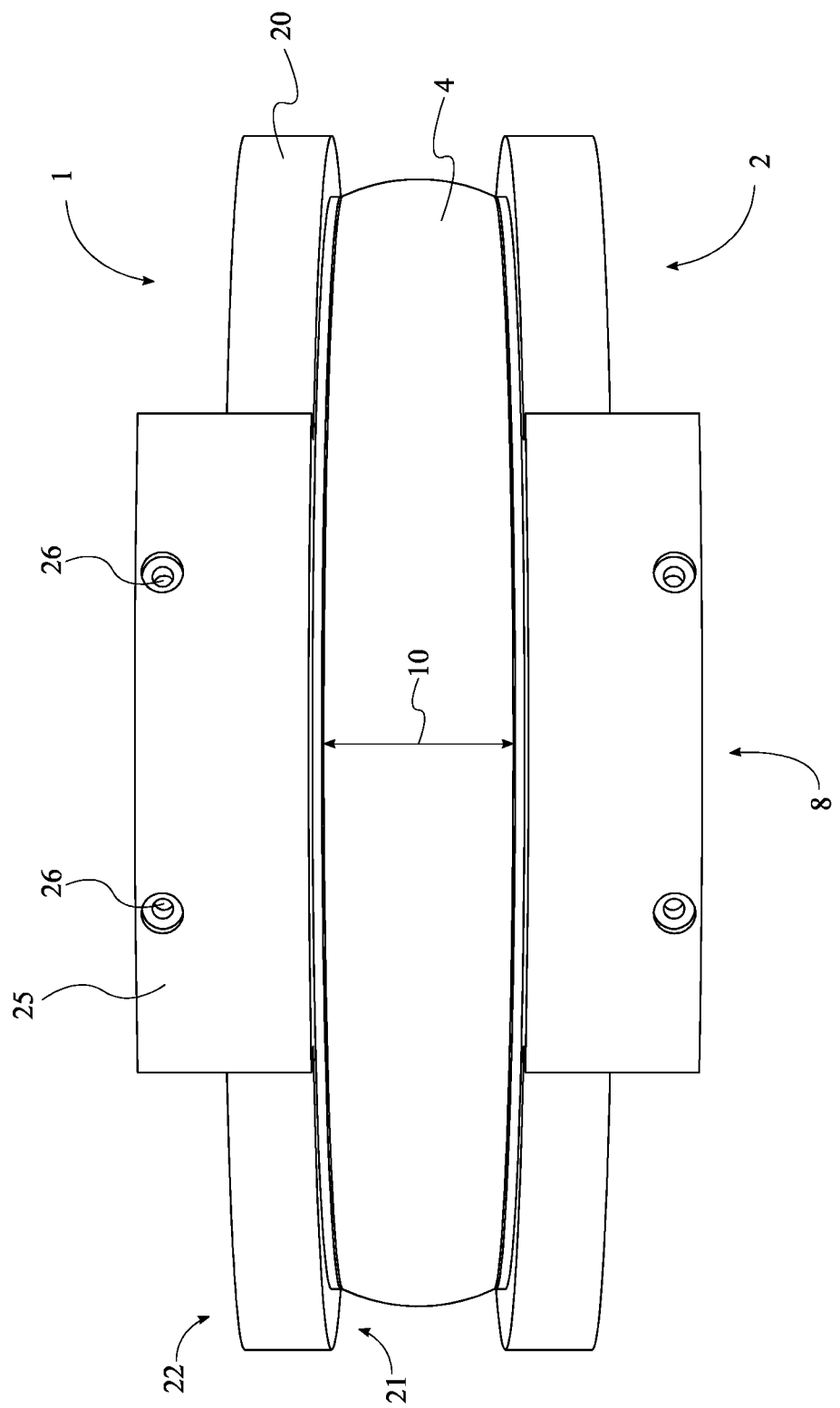
FIG. 4 is a rear view of the present invention.

In the preferred embodiment, the plate body 20 of the first end plate 1 and the plate body 20 of the second end plate 2 are oriented at a specified tilt angle 6 to each other, as illustrated in FIG. 1. The specified tilt angle 6 defines a deviation of the plate bodies of the first end plate 1 and second end plate 2 from being oriented parallel to each other. The specified tilt angle 6 may vary in different embodiments, mainly to correspond with different spinal disc types to replace. In various embodiments, the specified tilt angle 6 may range from 0.5 degrees to 15 degrees. In some embodiments, the specified tilt angle 6 may be less than 0.5 degrees. In some embodiments, the specified tilt angle 6 may be 0 degrees, such that the first end plate 1 and the second end plate 2 are oriented parallel to each other. In some embodiments, the specified tilt angle 6 may exceed 15 degrees.

The plate convexity 23 is centrally positioned on the outer side 22 of the plate body 20 for each of the first end plate 1 and the second end plate 2, similarly, the concavity 24 is centrally positioned on the inner side 21 of the plate body 20 for each of the first end plate 1 and the second end plate 2. In some embodiments, the thickness of the plate body 20 is constant, and the plate convexity 23 and the concavity 24 are formed through a deviation from the generally flat geometry of the plate body 20, such that the thickness of the end plates at the plate convexity 23 and concavity 24 is equal to the thickness of the end plates at their perimeter. In other embodiments, the plate convexity 23 and the concavity 24 of the first end plate 1 and the second end plate 2 may be formed independently of each other. In some embodiments, a fillet may be formed between the plate body 20 and the plate convexity 23 with a radius of, for example, but not limited to, a range from 0.015 inches to 0.5 inches. The fillet serves to reduce any polymeric stress due to vertical localized compression forces on the first and second end plates 2. The first core convexity 30 is positioned within the concavity 24 of the first end plate 1, and the second core convexity 31 is positioned within the concavity 24 of the second end plate 2.

As previously mentioned, in some embodiments, the outer core 4 is connected between the first end plate 1 and the second end plate 2 through the plurality of interlocking members 5. In some embodiments, the inner core 3 is further connected between the first end plate 1 and the second end plate 2 in the same manner through the plurality of interlocking members 5, though this is not considered a requirement. More particularly, the inner side 21 of the first end plate 1 is connected to the outer core 4 through the plurality of interlocking members 5, and the inner side 21 of the second end plate 2 is connected to the outer core 4 opposite the first end plate 1 axially along the inner core 3 through the plurality of interlocking members 5.

In some embodiments, the first end plate 1 and the second end plate 2 each further comprise an attachment flange 25 and at least one fastener aperture 26, as shown in FIGS. 1-6. The attachment flange 25 may be used to anchor the present invention to adjoining vertebrae through one or more implant screws. The inclusion of the attachment flange 25 in various embodiments will depend on end product requirements. The attachment flange 25 is perpendicularly and perimetrically connected to the plate body 20, and extends away from the inner side 21, past the outer side 22 for each of the first end plate 1 and the second end plate 2, wherein the attachment flange 25 is connected along a flange arc segment of the perimeter of the plate body 20. Preferably, the attachment flange 25 does not extend past the inner side 21, though this may vary in different embodiments. The at least one fastener aperture 26 traverses through the attachment flange 25 for each of the first end plate 1 and the second end plate 2. Each of the at least one fastener aperture 26 may be a counterbore hole, a countersink hole, a through hole, or other types of holes suitable for receiving various fasteners in different embodiments.

Furthermore, in some embodiments, the attachment flange 25 comprises an inner groove 27. The inner groove 27 traverses into and radially through the attachment flange 25 along the flange arc segment adjacent to the outer side 22 of the plate body 20 and adjacent to a perimeter of the plate body 20 for each of the first end plate 1 and the second end plate 2. The inner groove 27 serves to provide clearance to the edge of adjoining vertebra where the total disc replacement is being performed to reduce any wear from vertebral edges.

In the preferred embodiment, referring to FIGS. 2 and 5-7, the outer core 4 comprises a first plurality of core interlocking members 50 and a second plurality of core interlocking members 51 from the plurality of interlocking members 5, wherein the first plurality of core interlocking members 50 and the second plurality of core interlocking members 51 are positioned opposite each other along a thickness of the outer core 4. In some embodiments, the first plurality of core interlocking members 50 and the second plurality of core interlocking members 51 are positioned axially opposite each other along the thickness of the outer core. Further, the first end plate 1 and the second end plate 2 each further comprise a plurality of plate interlocking members 52 from the plurality of interlocking members 5. The plurality of plate interlocking members 52 is positioned concentrically around the concavity 24 on the inner side 21 of the plate body 20 for each of the first end plate 1 and the second end plate 2. The first plurality of core interlocking members 50 of the outer core 4 is engaged with the plurality of plate interlocking members 52 of the first end plate 1, and the second plurality of core interlocking members 51 of the outer core 4 is engaged with the plurality of plate interlocking members 52 of the second end plate 2.

Figure 8:
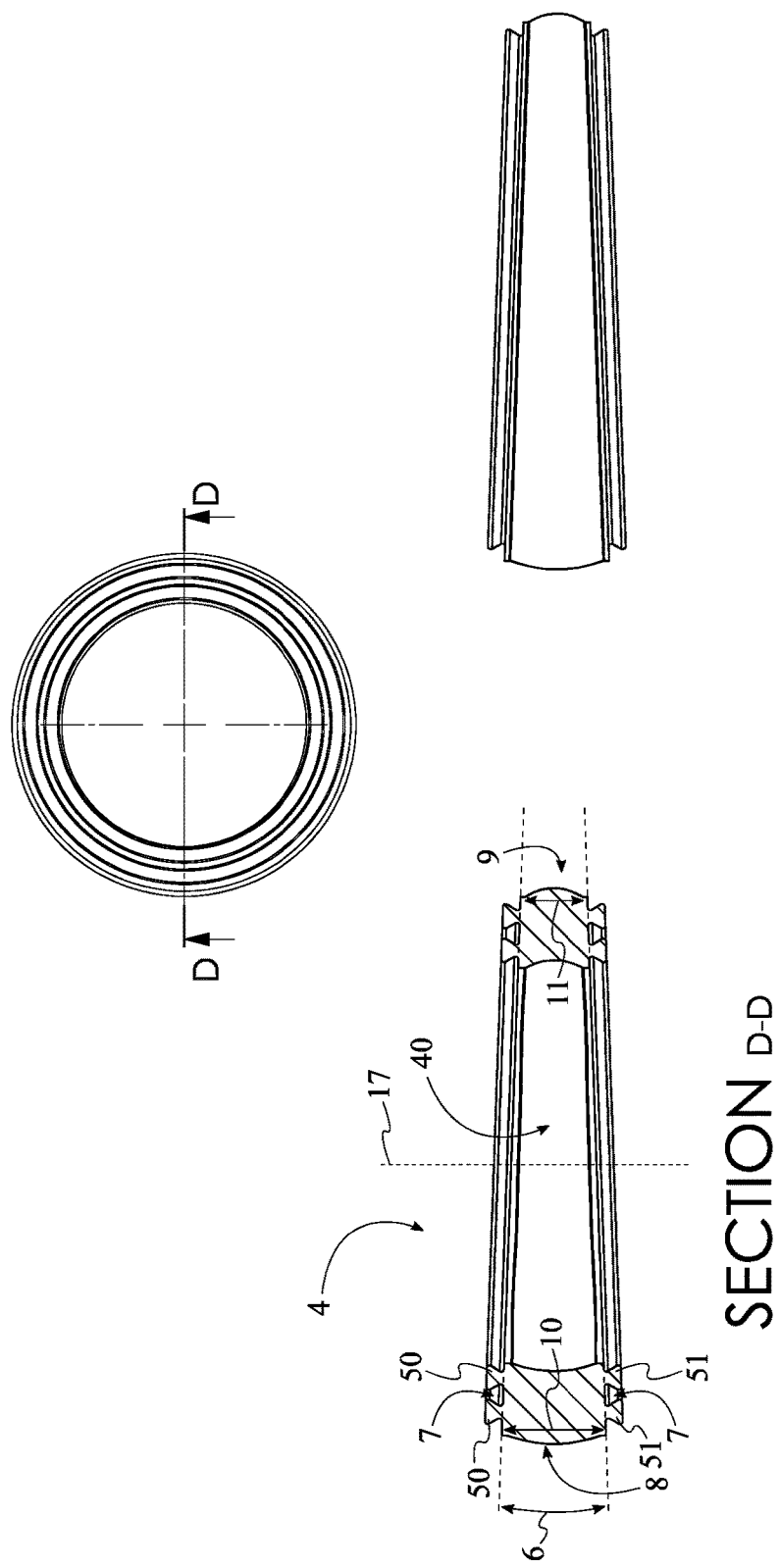
FIG. 8 is a top view, a side sectional view, and a side view of the outer core of the present invention.
Figure 9:
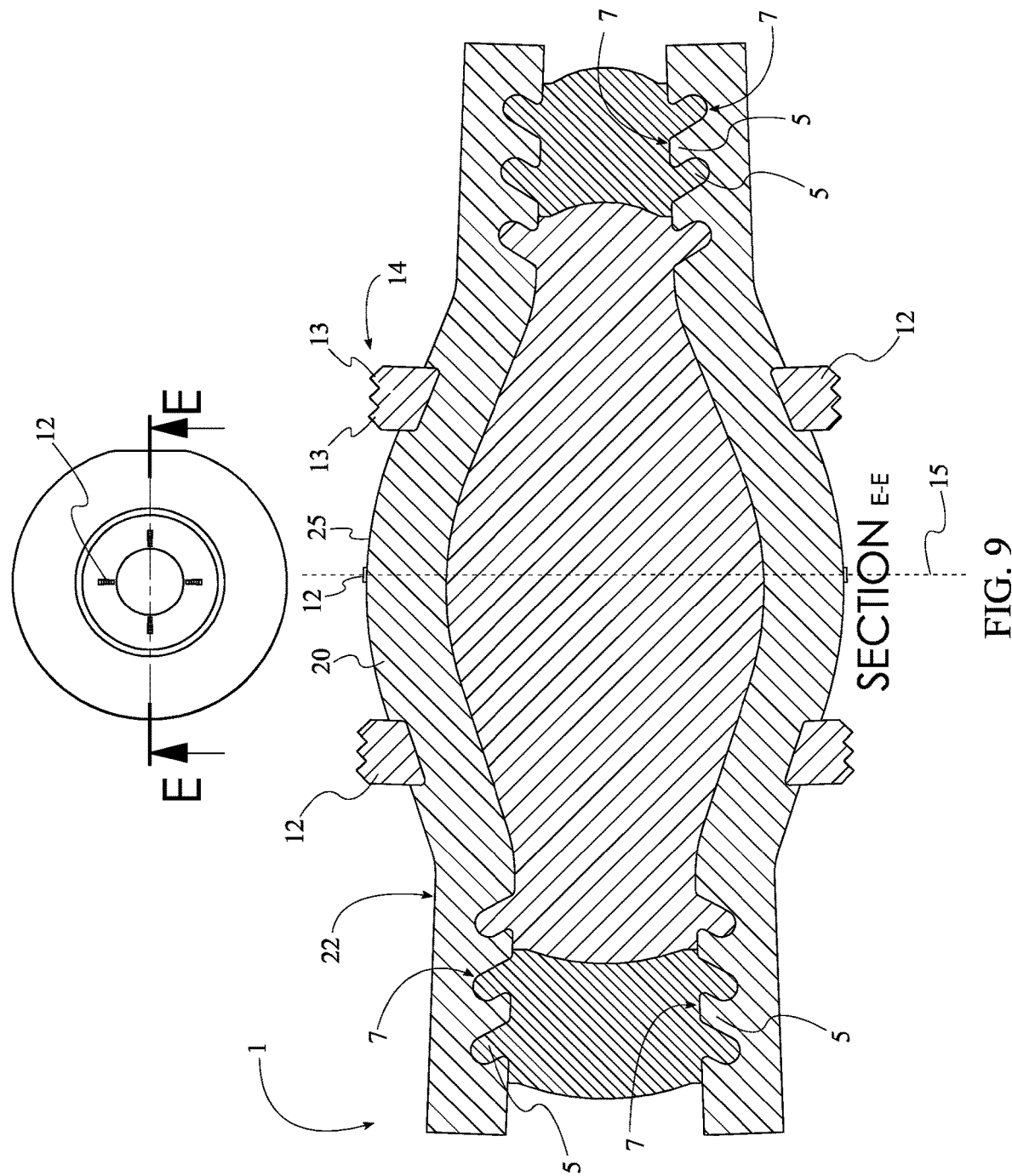
FIG. 9 is a top view and a side sectional view of an alternative embodiment of the present invention incorporating anchoring protrusions.

Furthermore, in some embodiments, the present invention further comprises a plurality of interlocking member receiving channels 7, as shown in FIGS. 2, 5, 6, and 8-11. Each of the plurality of interlocking member receiving channels 7 is positioned concentrically with and adjacent to one of the plurality of interlocking members 5, and each of the plurality of interlocking members 5 is positioned within one of the plurality of interlocking member receiving channels 7. The plurality of interlocking members 5 and the plurality of interlocking member receiving channels 7 are configured to resist extrusion of the inner core 3 and outer core 4 when the inner core 3 and outer core 4 are subject to external forces. The specific configuration and shape of the plurality of interlocking members 5 and the plurality of interlocking member receiving channels 7 may vary in different embodiments. For example, in some embodiments, the plurality of interlocking members 5 and the plurality of interlocking member receiving channels 7 have a dovetail mating configuration as shown in FIGS. 2 and 5-8, wherein a cross section width of each of the plurality of interlocking members 5 increases with distance away from the axial center of the outer core 4, and wherein each of the plurality of interlocking member receiving channels 7 is shaped inversely to the plurality of interlocking members 5 to accommodate them. In some embodiments, a cross section of each of the plurality of interlocking members 5 resembles a "tooth", having an angled protrusion with a circular element at the end, wherein the cross section of the interlocking member receiving channels 7 would have correspondingly negative geometry to receive the tooth. In either case, the distal geometry of the interlocking members 5 has a greater radial width than the remainder of the interlocking members 5, facilitating securement of the interlocking members 5 within the interlocking member receiving channels 7. Alternatively, in some embodiments, the interlocking members 5 and receiving channels 7 may not vary in thickness, as shown in FIG. 9.

Figure 10:
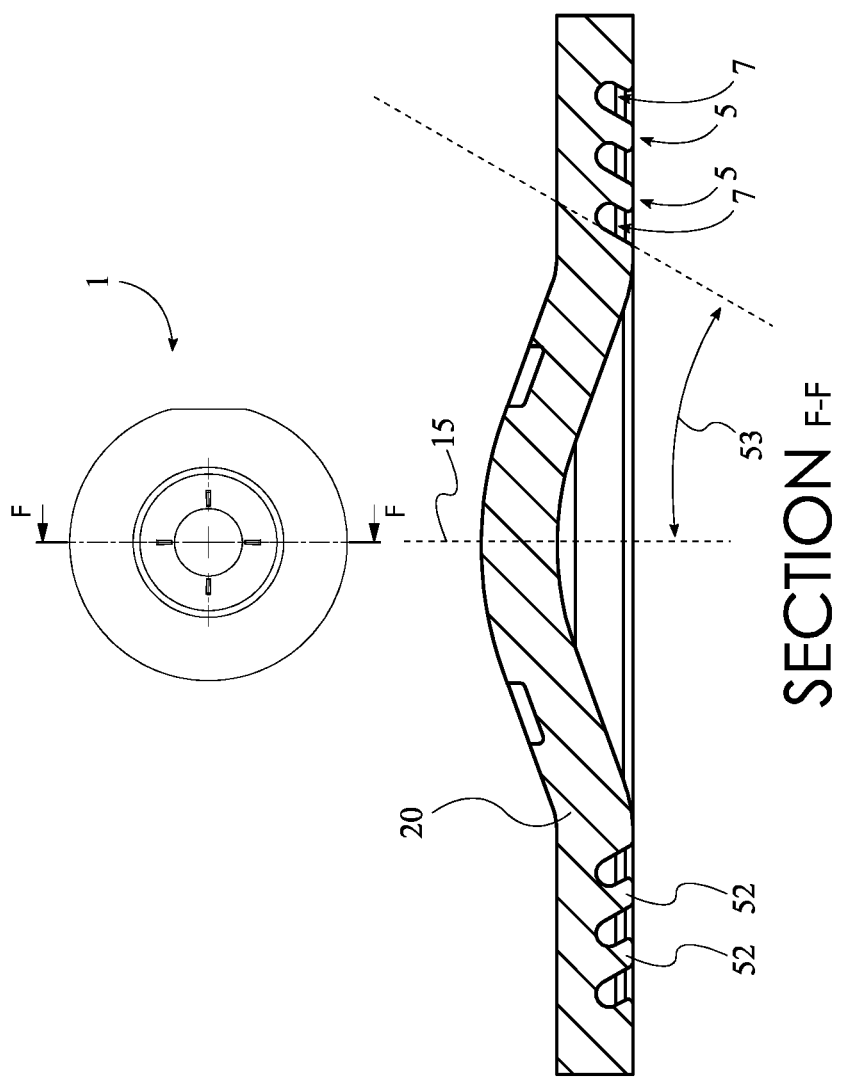
FIG. 10 is a top view and a side sectional view of one of the end plates in the alternate embodiment.
Figure 11:
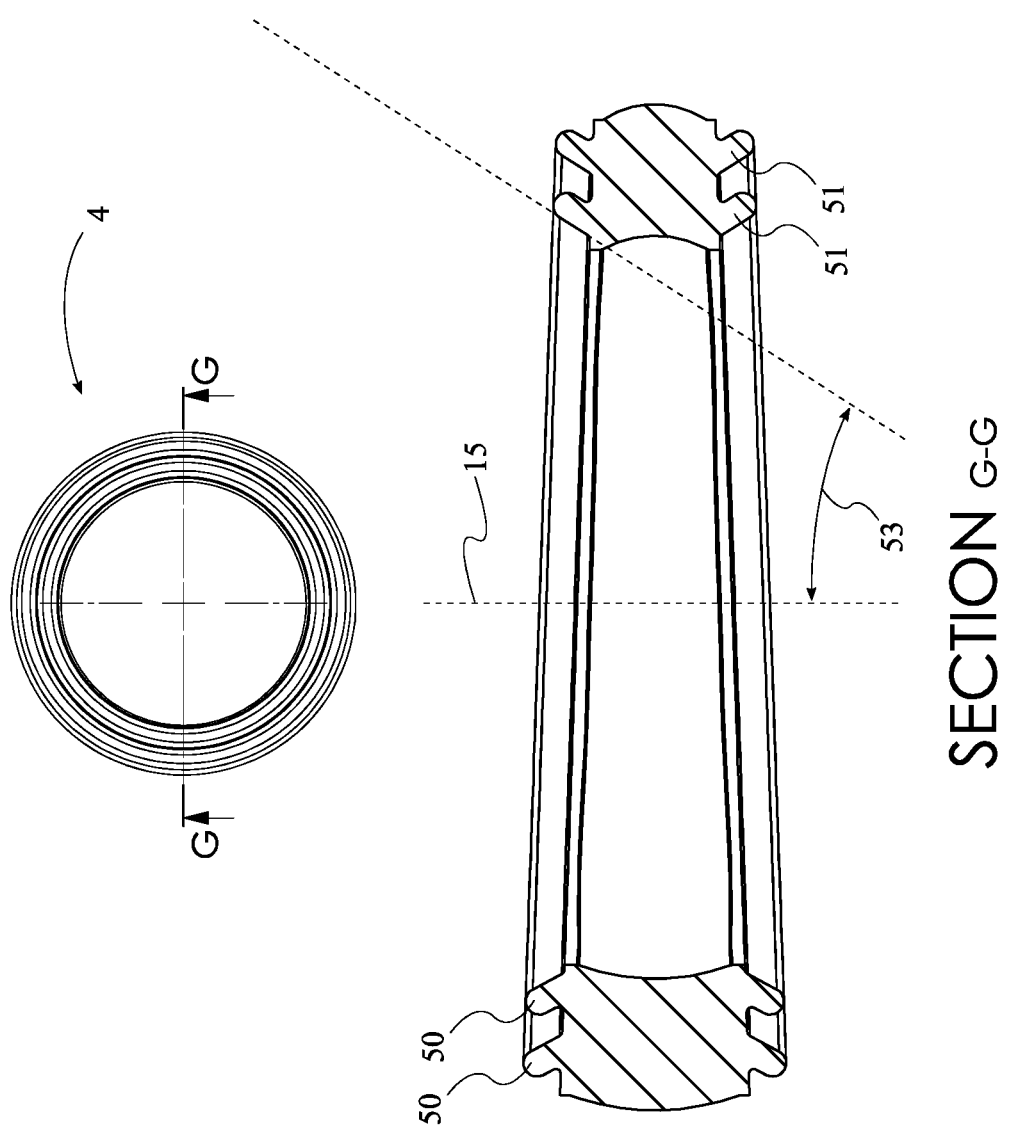
FIG. 11 is a top view and a side sectional view of the outer core in the alternate embodiment.
Figure 12:
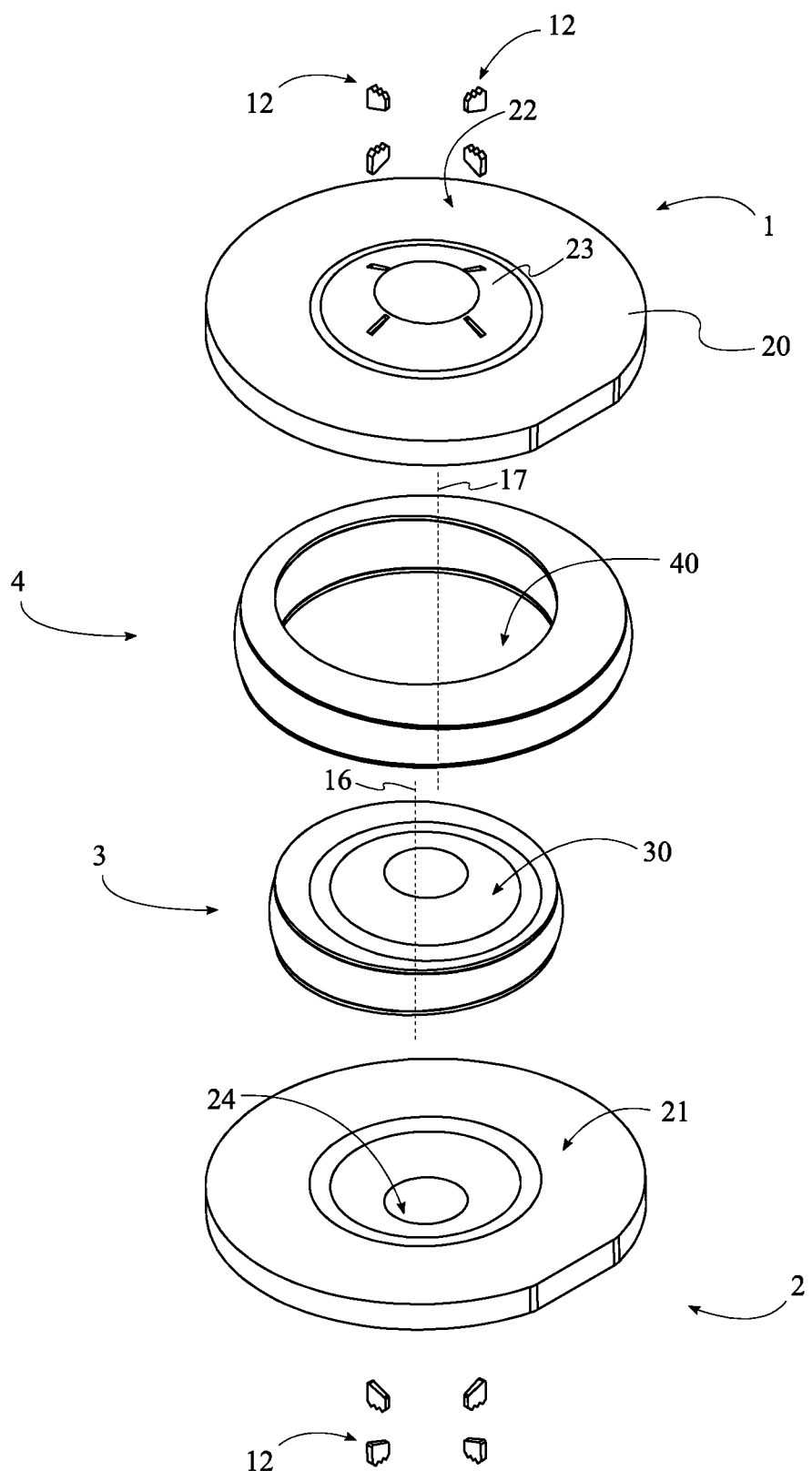
FIG. 12 is an exploded perspective view of a second alternate embodiment of the present invention.
Figure 13:
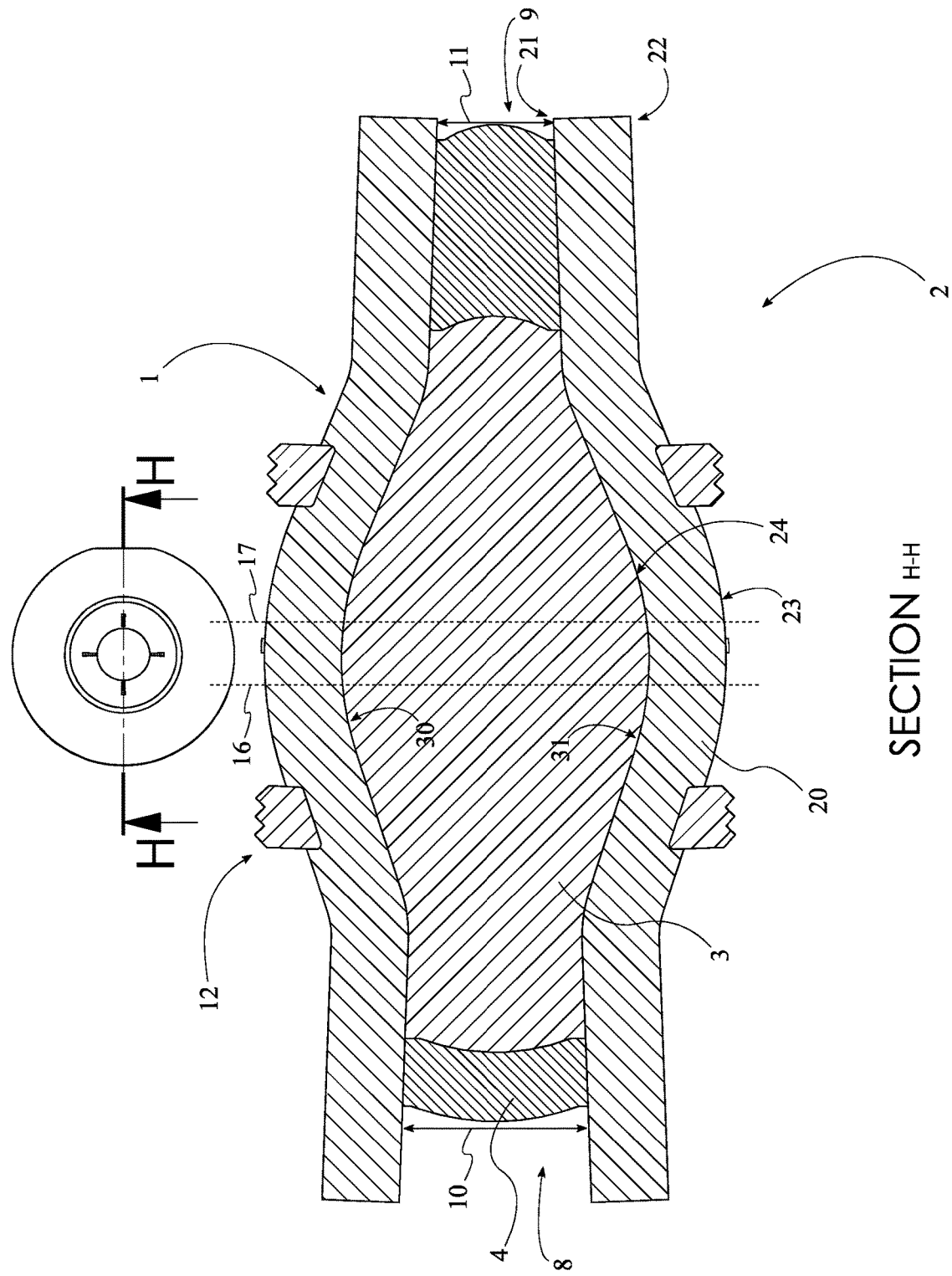
FIG. 13 is a top view and a side sectional view of the second alternate embodiment.
Figure 14:
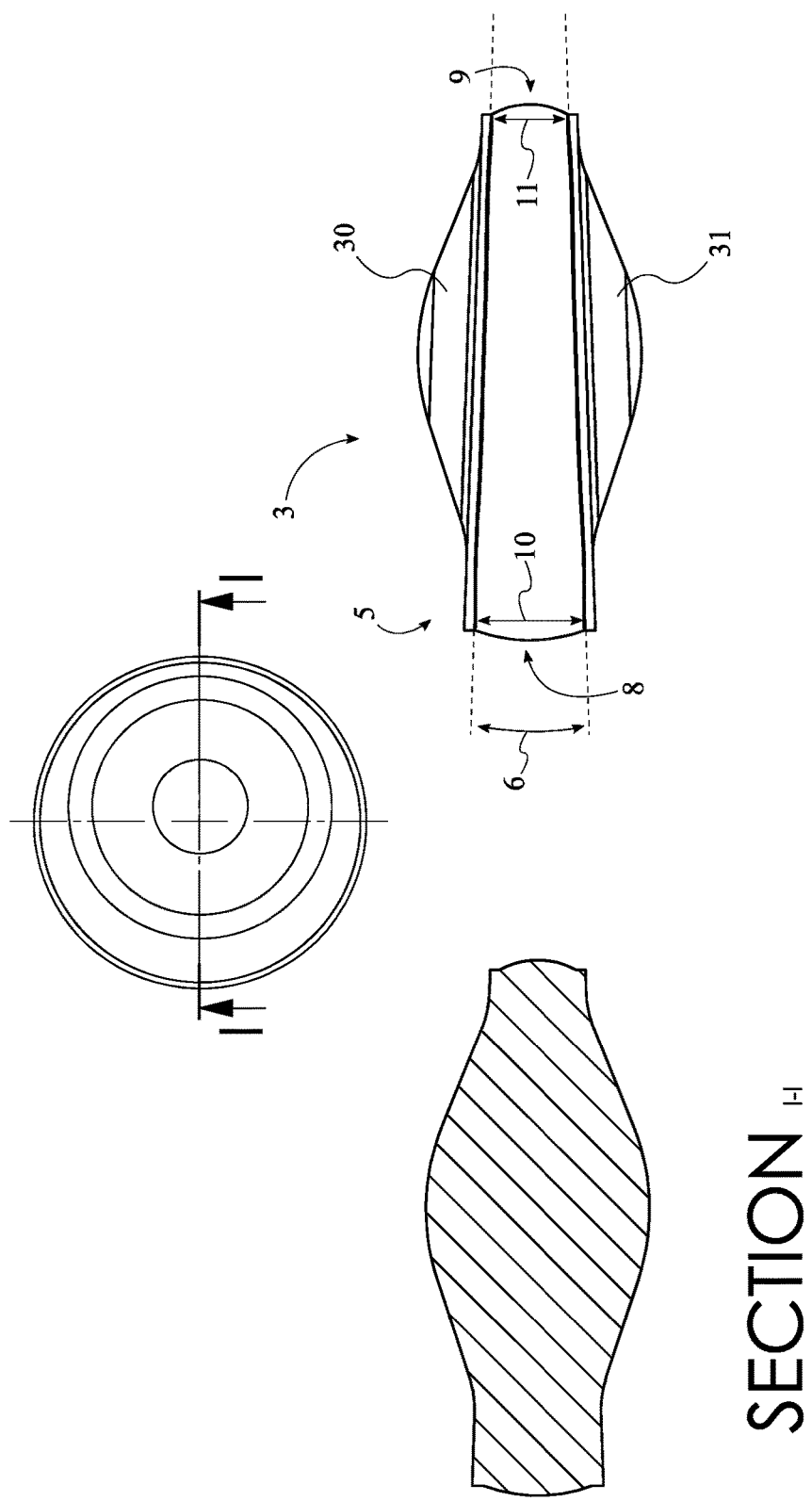
FIG. 14 is a top view, a side sectional view, and a side view of the inner core of the second alternate embodiment.
Figure 15:
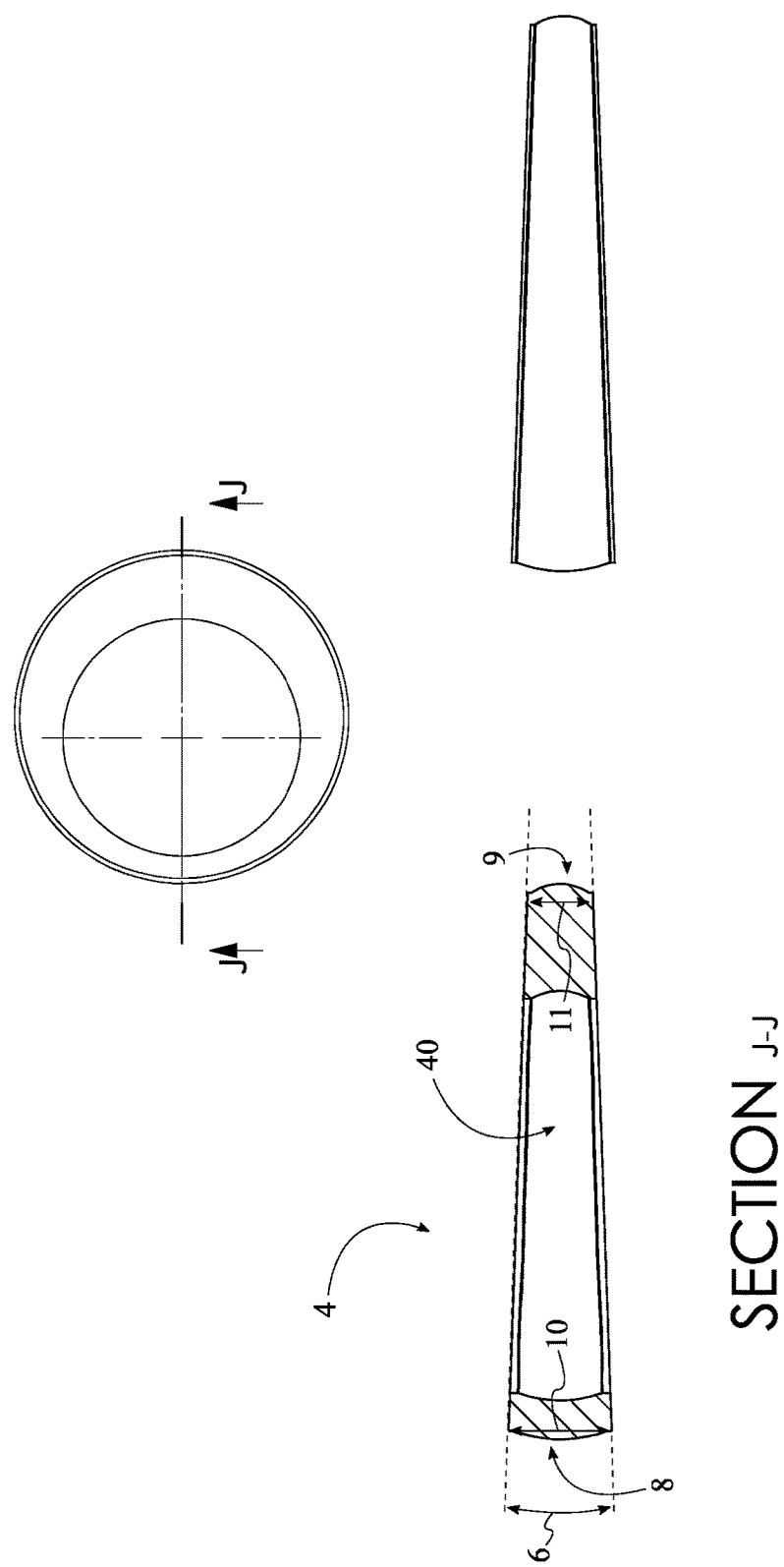
FIG. 15 is a top view, a side sectional view, and a side view of the outer core of the second alternate embodiment.
Figure 16:
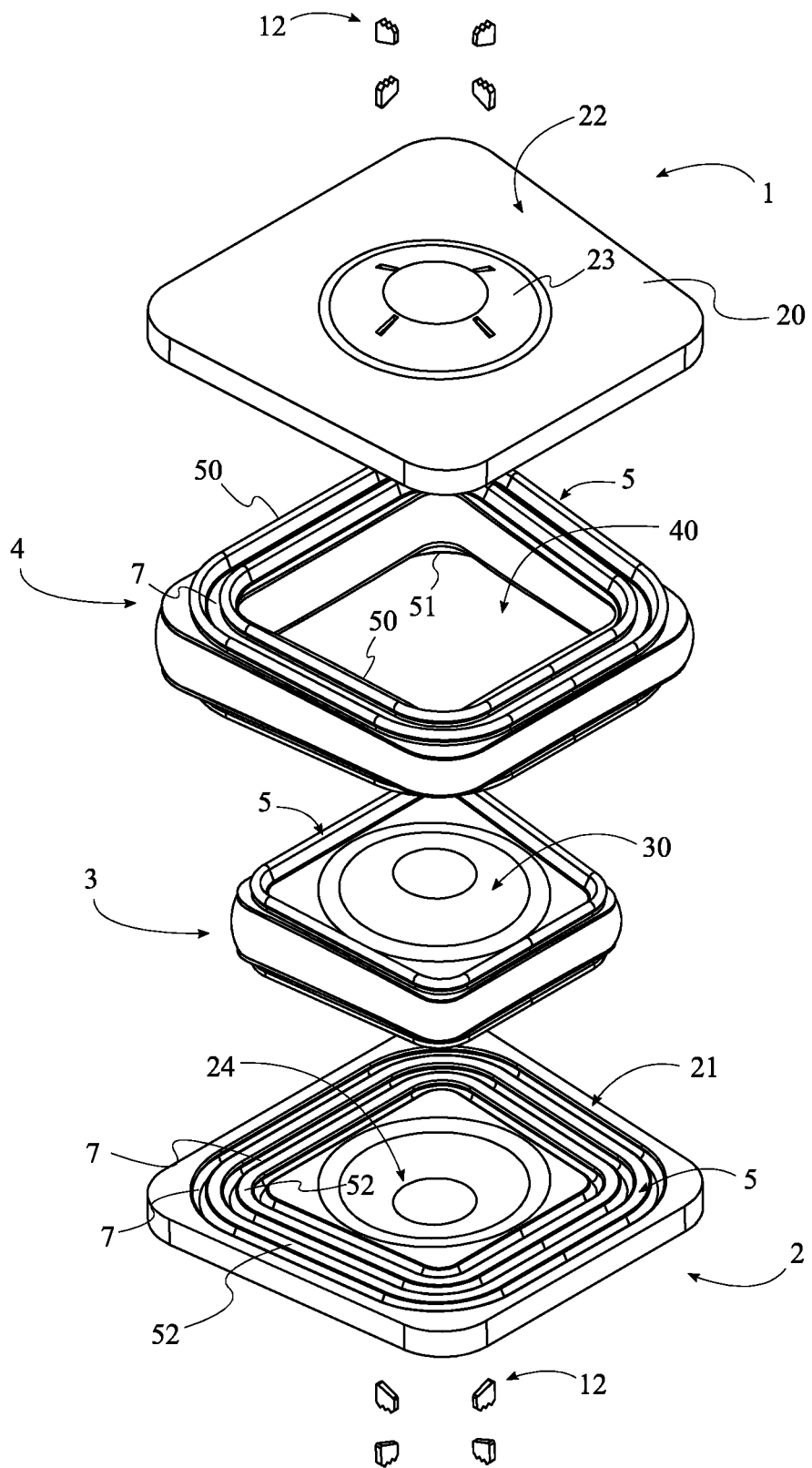
FIG. 16 is an exploded perspective view of a third alternate embodiment of the present invention.
Figure 17:
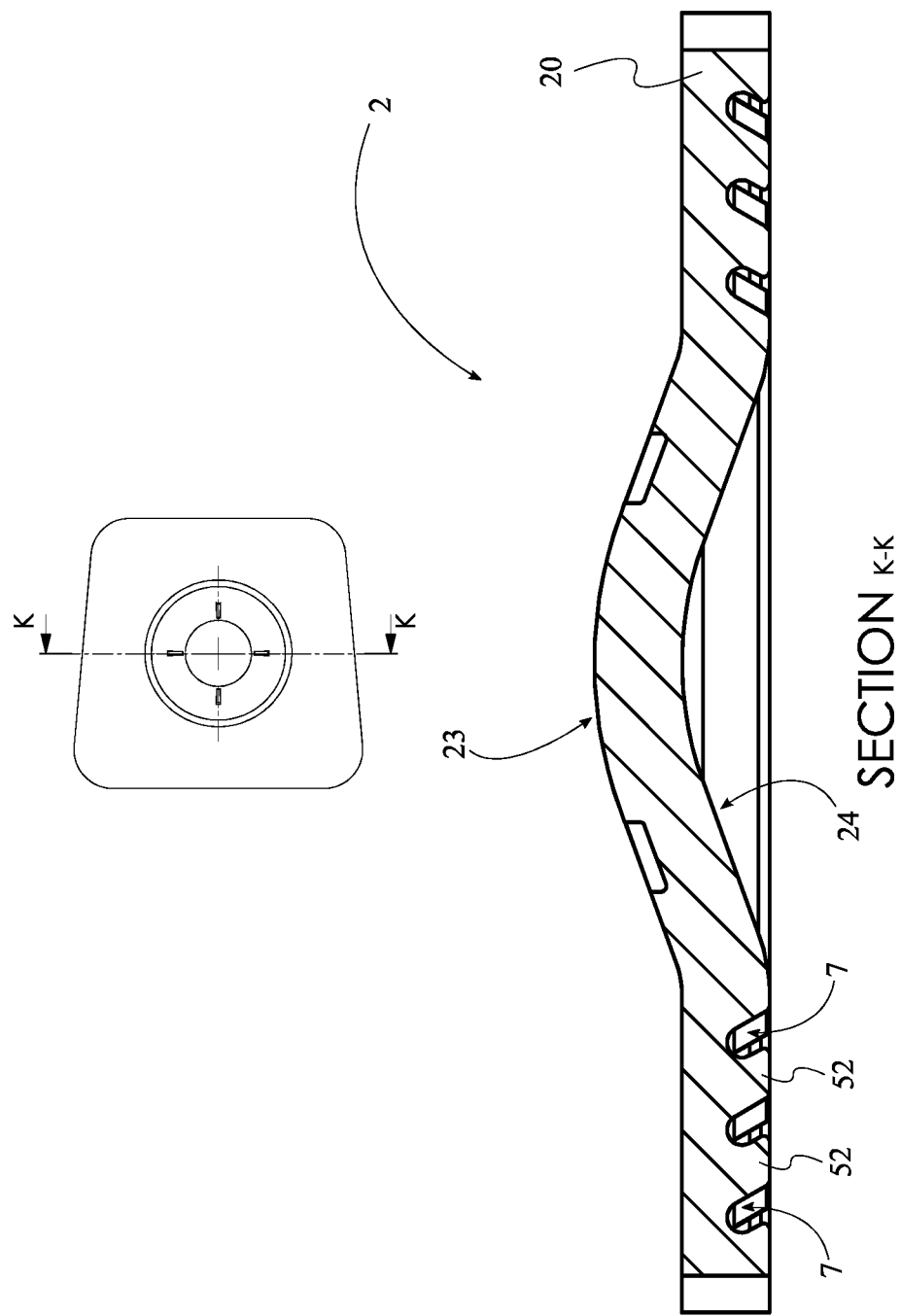
FIG. 17 is a top view and a side sectional view of one of the end plates of the third alternate embodiment.
Figure 18:
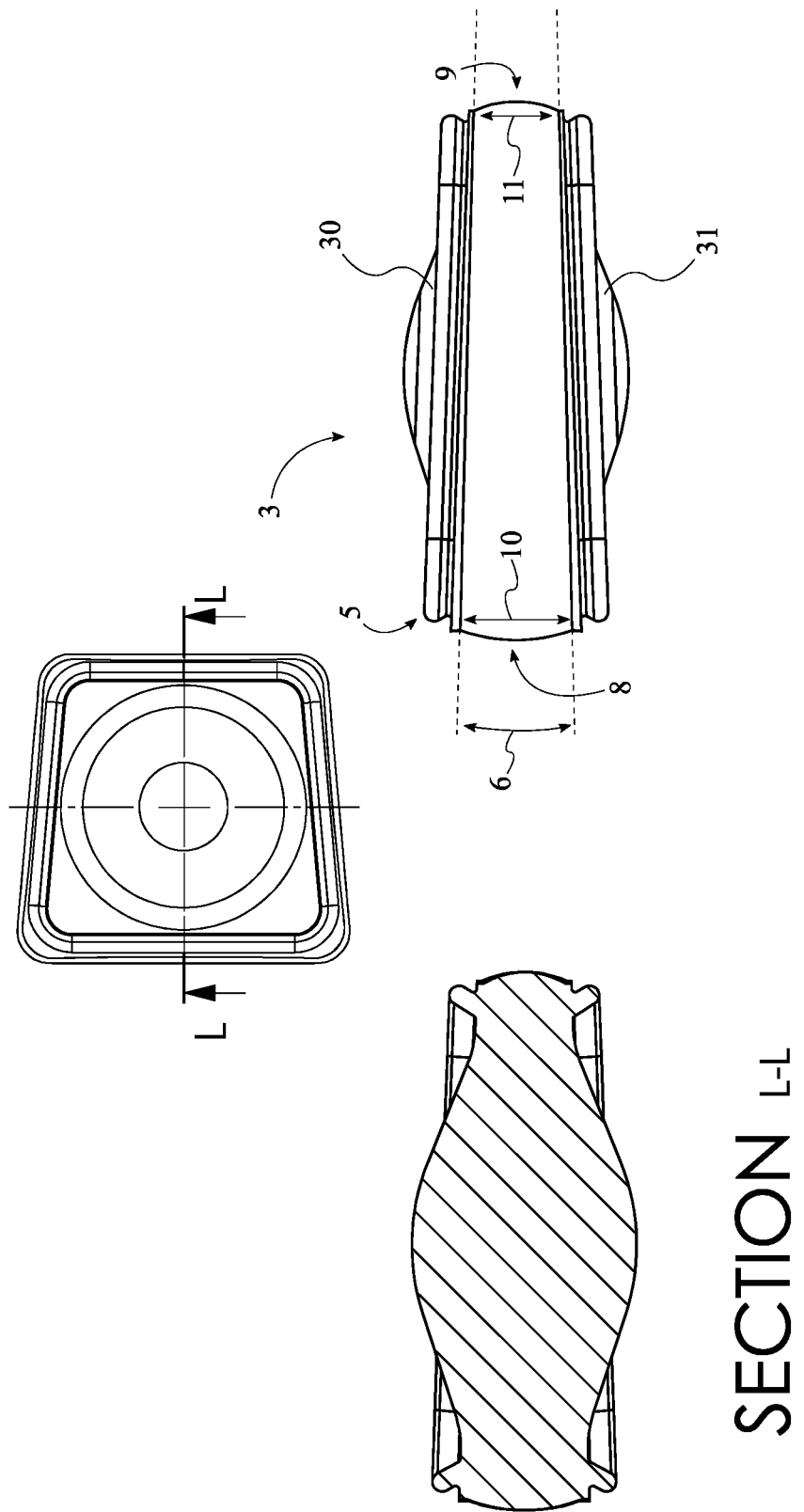
FIG. 18 is a top view, a side sectional view, and a side view of the inner core of the third alternate embodiment.
Figure 19:
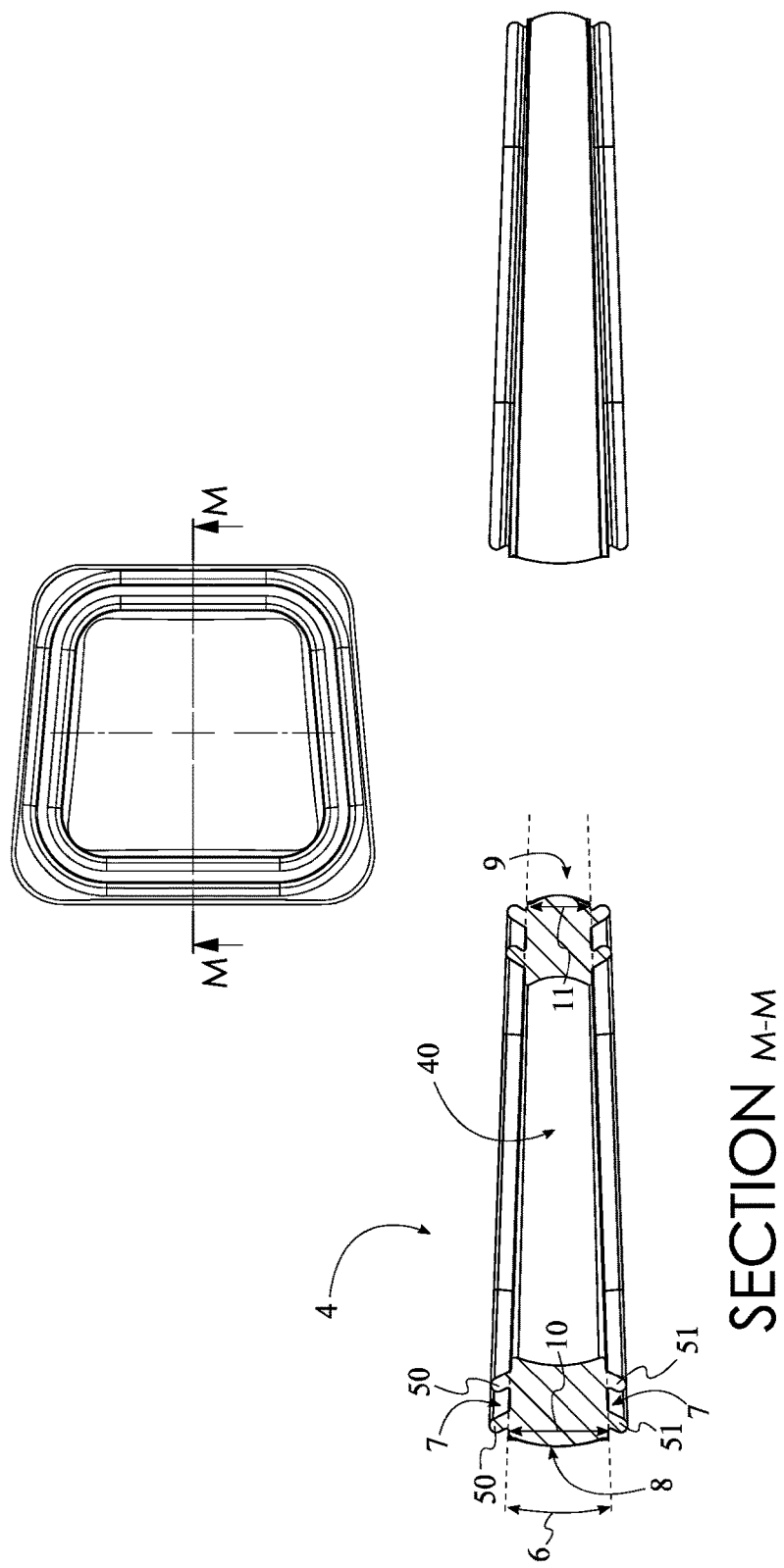
FIG. 19 is a top view, a side sectional view, and a side view of the outer core of the third alternate embodiment.
Figure 20:
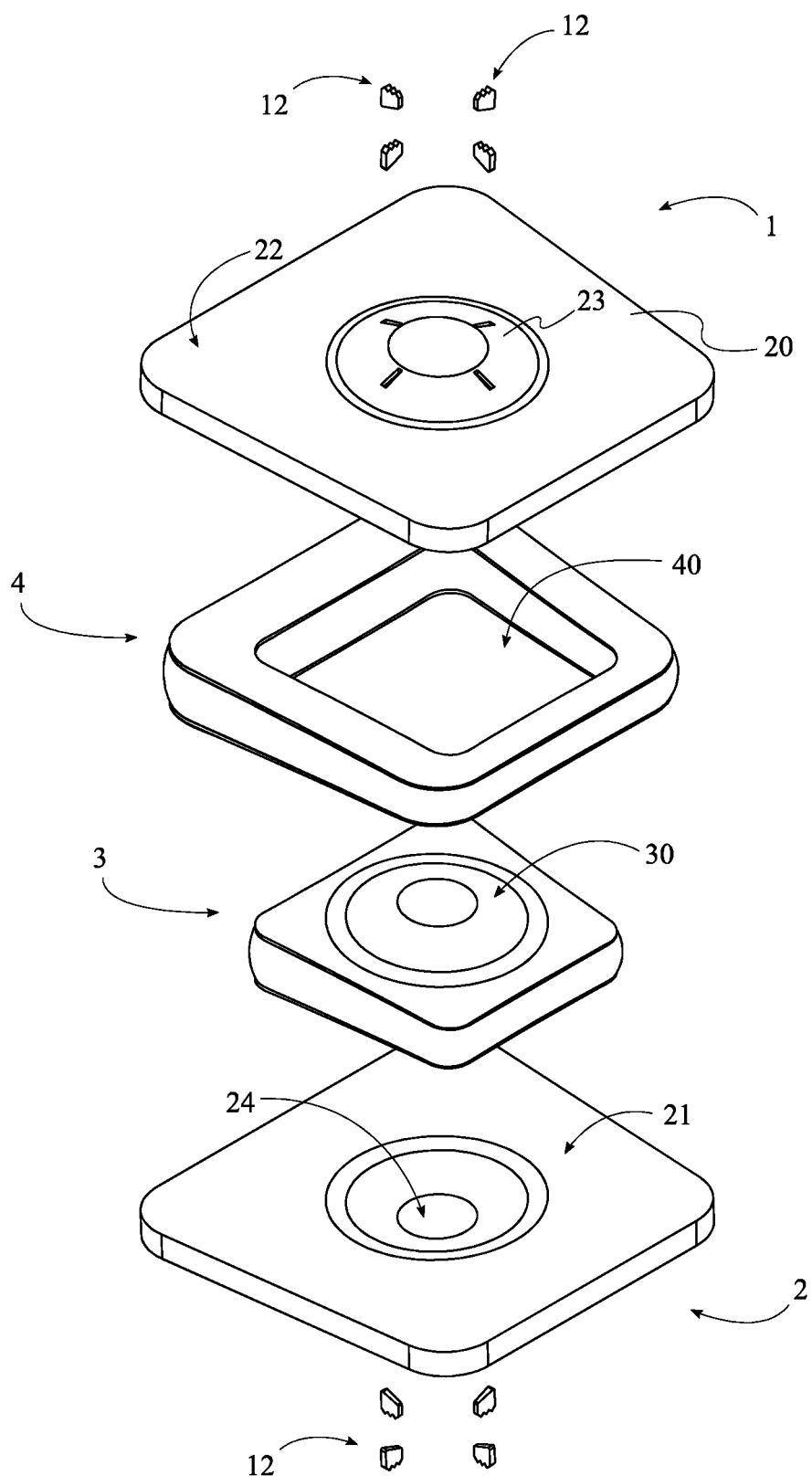
FIG. 20 is an exploded perspective view of a fourth alternate embodiment of the present invention.
Figure 21:
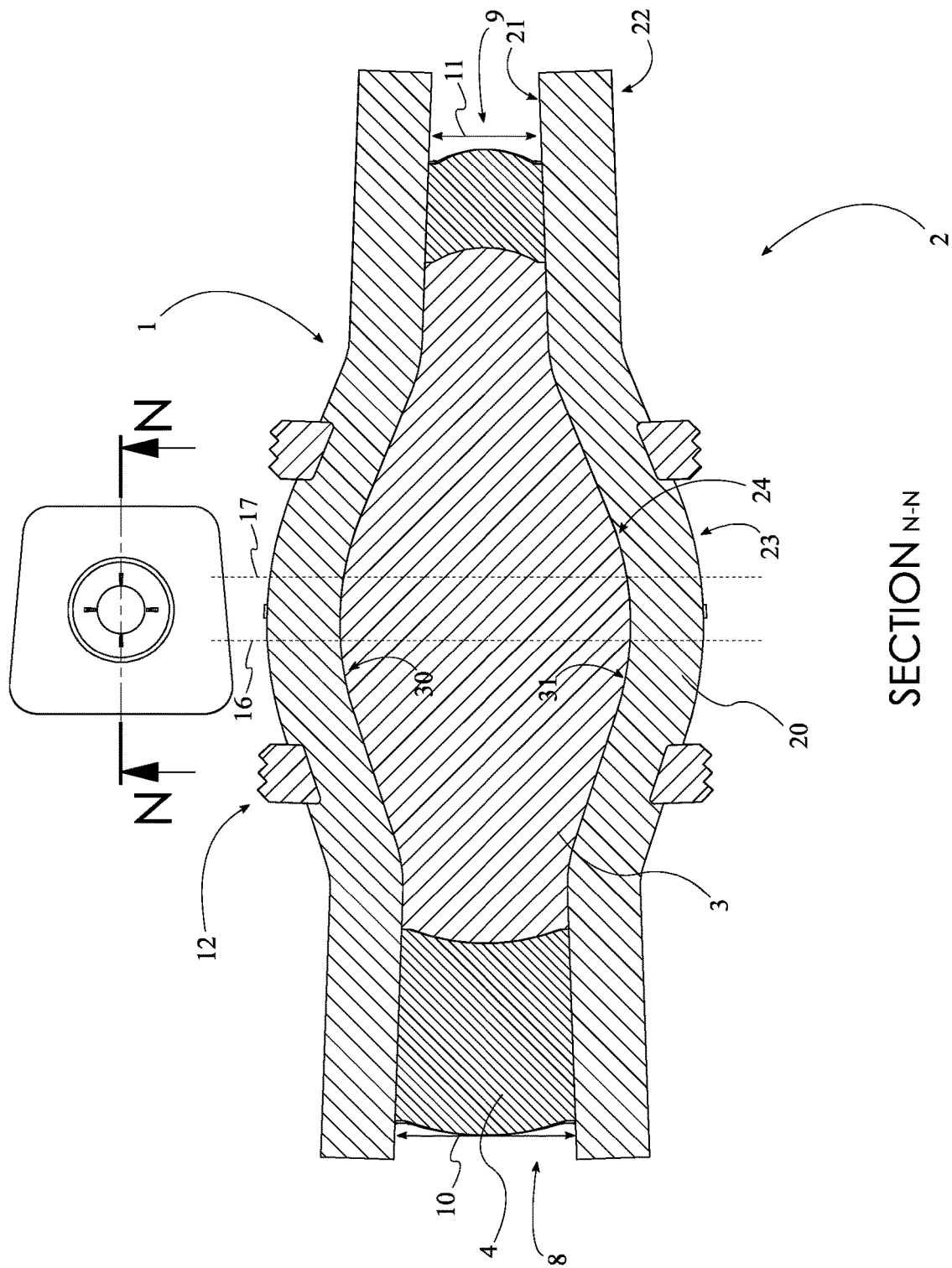
FIG. 21 is a top view and a side sectional view of the fourth alternate embodiment.
Figure 22:
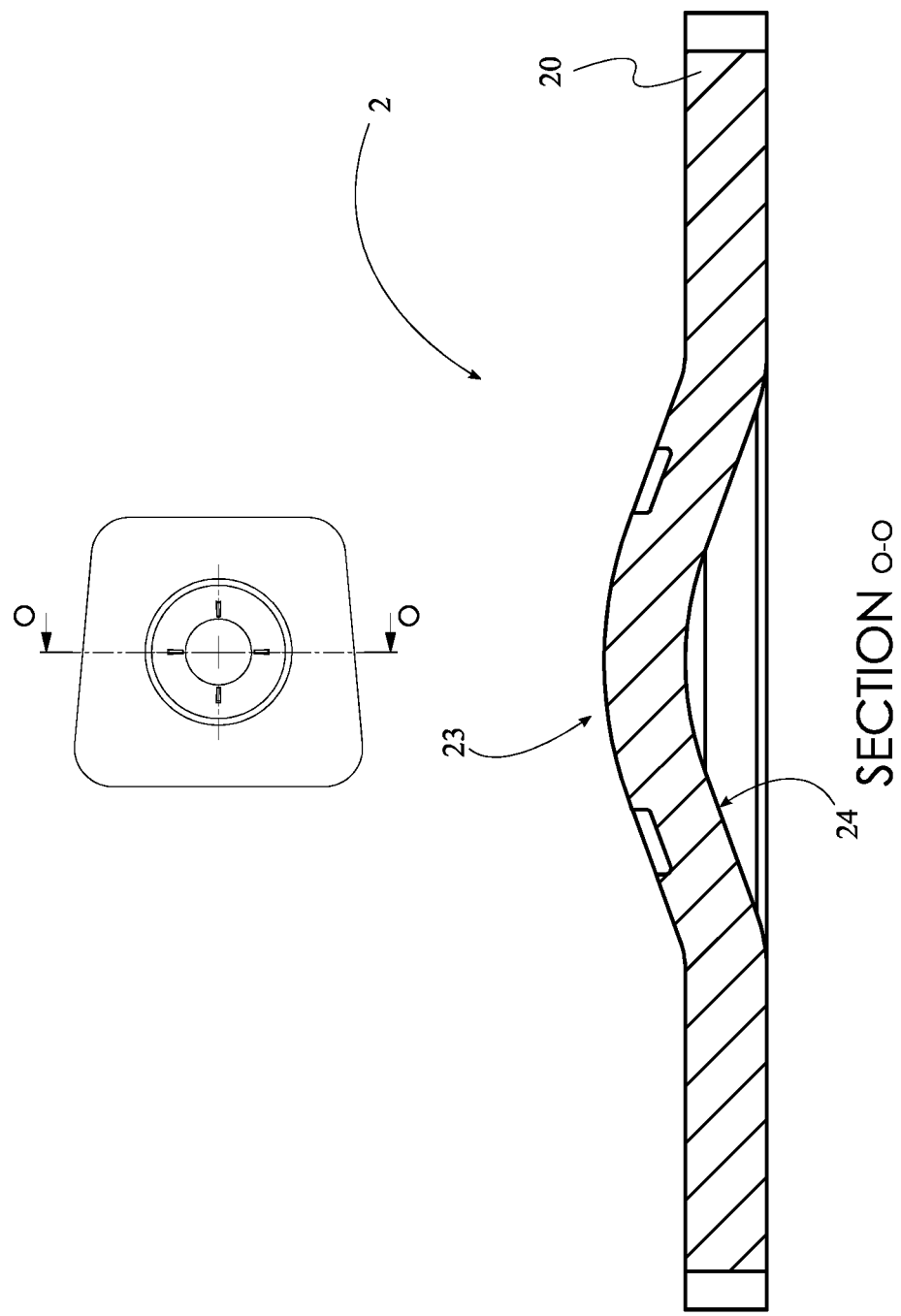
FIG. 22 is a top view and a side sectional view of one of the end plates of the fourth alternate embodiment.
Figure 23:
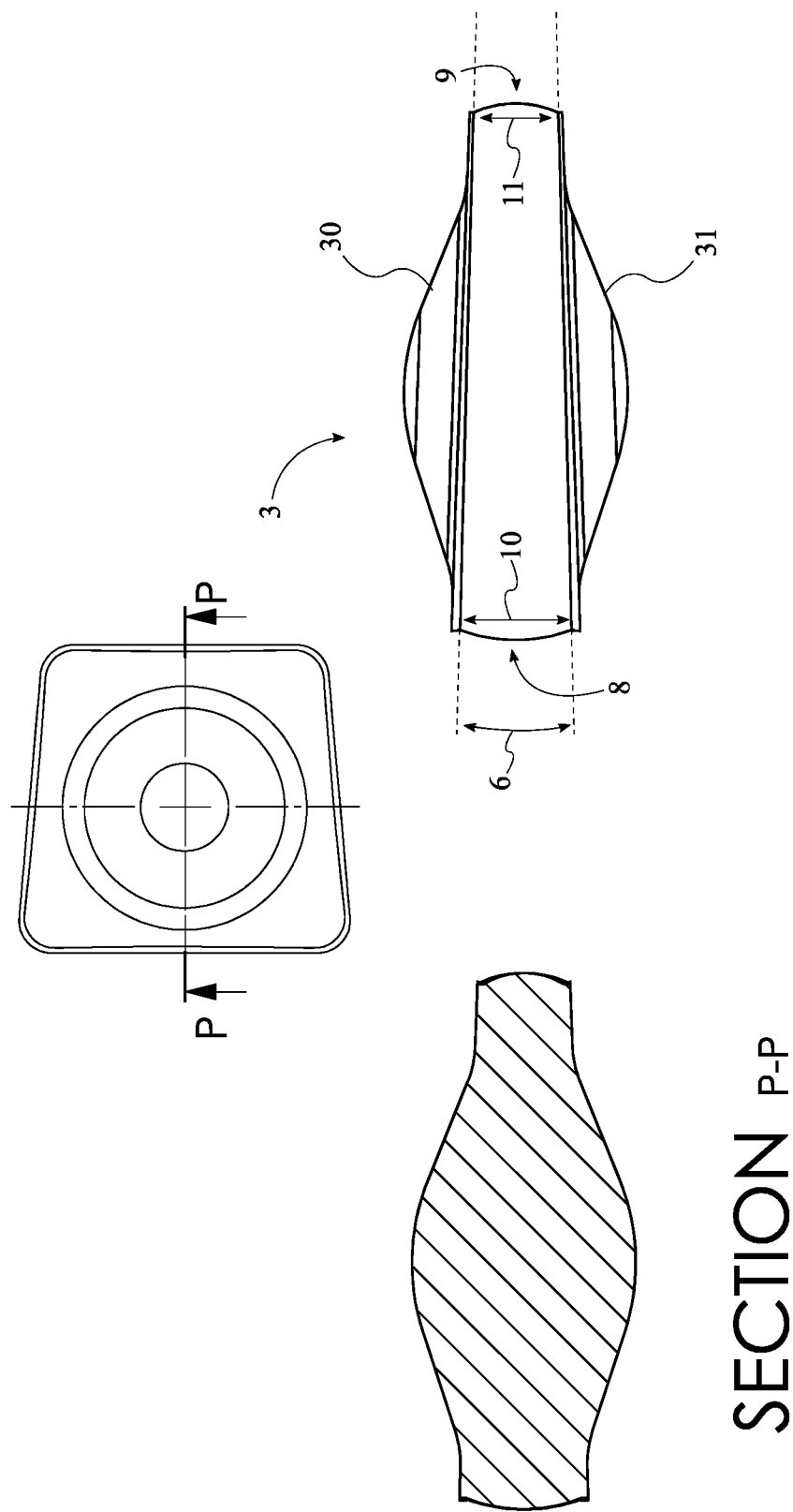
FIG. 23 is a top view, a side sectional view, and a side view of the inner core of the fourth alternate embodiment.
Figure 24:
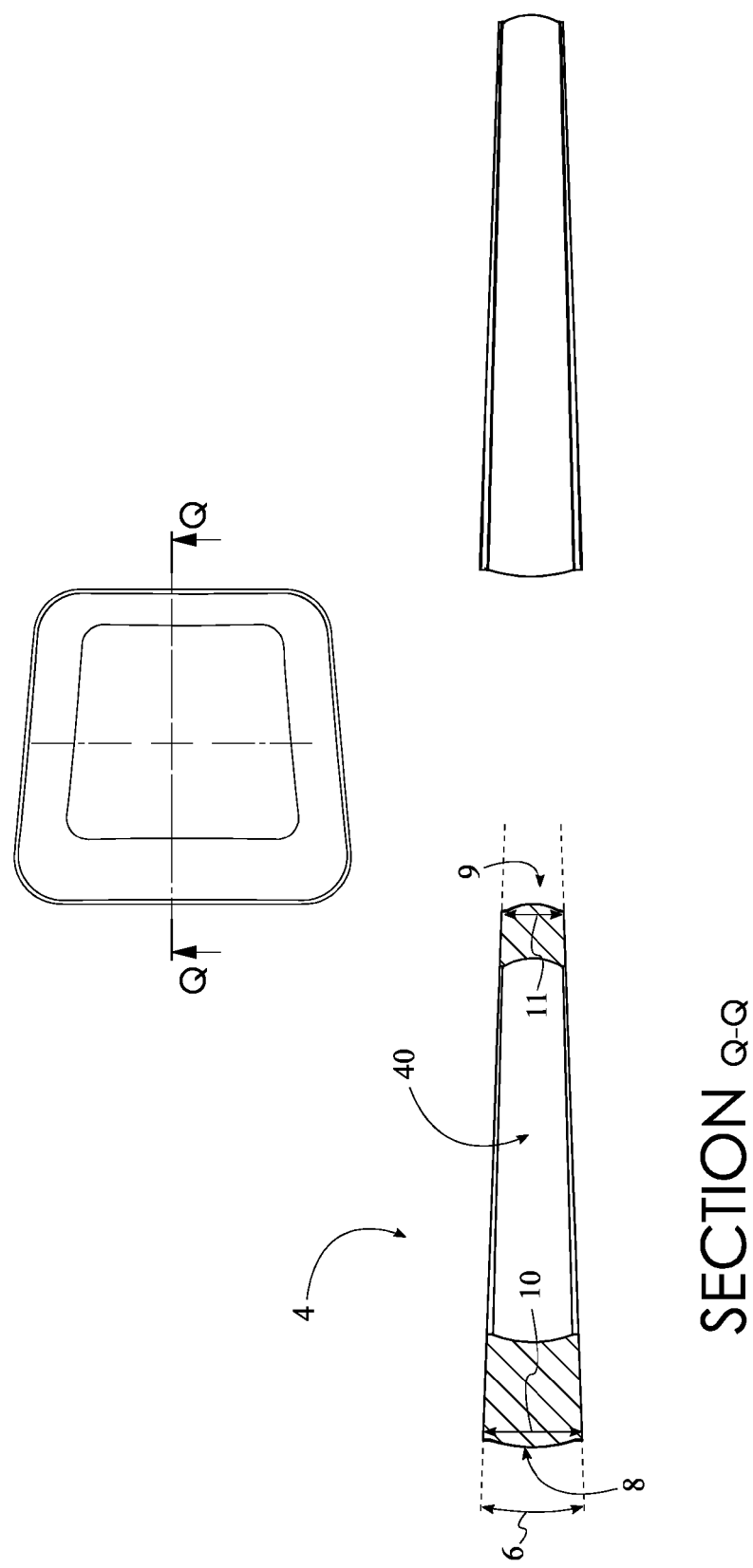
FIG. 24 is a top view, a side sectional view, and a side view of the outer core of the fourth alternate embodiment.

More particularly, FIGS. 9-11 illustrate an alternative embodiment wherein each of the plurality of interlocking members 5 is oriented at a specified anti-extrusion angle 53 in order to adequately resist extrusion of the inner core 3 and/or outer core 4 as previously described. In such an embodiment. More particularly, each of the first plurality of core interlocking members 50, the second plurality of core interlocking members 51, and the plurality of plate interlocking members 52 is oriented at the specified anti-extrusion angle 53. The specified anti-extrusion angle 53 may be defined in various ways, but herein the specified anti-extrusion angle 53 is defined in relation to a central axis 15 of the present invention. The central axis 15 may be considered to be an axis about which the radial features of the present invention, such as, but not limited to the inner core 3 and the outer core 4, and the plate body 20 are positioned concentrically about. Separate central axes may be defined as appropriate for the inner core 3, outer core 4, and plate body 20 in order to account for any angular discrepancies due to the specified tilt angle 6. The previously discussed inner core centerline 16 and outer core centerline 17 may, in various embodiments, be the same as or distinct from the central axis 15.

It may be understood herein that due to the specified tile angle 6, true central axes of the plate body 20, inner core 3, and/or outer core 4 may not be positioned exactly coincidental with each other. However, that is considered to be the case herein for the sake of simplicity.

It is important to define herein that the specified anti-extrusion angle 53 should be oriented radially outward from the central axis, such that an imaginary line extending outward from any given member of the first plurality of core interlocking members 50 or the second plurality of core interlocking members 51 does not intersect with the central axis. This is important because an inwardly-oriented anti-extrusion angle 53 would not be effective or as effective and may not provide effective interlock as an outwardly-oriented anti-extrusion angle.

As previously mentioned, the plurality of interlocking members 5 and the plurality of interlocking member receiving channels 7 function primarily to secure the inner core 3 to the first end plate 1 and the second end plate 2, but also secondarily to resist extrusion of the outer core 4 (and inner core 3, in applicable embodiments) when the present invention is subjected to external forces, compressive forces in particular. When the present invention is subjected to an axial compressive force, the inner core 3 and outer core 4 will tend to deform a certain amount in compression axially and in expansion laterally. Thus, is it a concern that subject to such forces, portions of the inner core 3 and outer core 4 will "extrude" out of their designated positions and potentially become misaligned or damaged. The plurality of interlocking member receiving channels 7 may function to provide some space to accommodate such extrusion, and moreover the physical interlocking between the interlocking members 5 and interlocking member receiving channels 7 prevents the inner core 3 and outer core 4 from becoming dislodged from their positions relative to the first end plate 1 and the second end plate 2. The quantity of both the plurality of interlocking members 5 and the plurality of interlocking member receiving channels 7 may vary in different embodiments, from 1 to 9, for example, though any quantity of interlocking members 5 and interlocking member receiving channels 7 may be included as desired in various embodiments.

As previously mentioned, in various embodiments, the first end plate 1 and the second end plate 2 may be oriented at a specified tilt angle 6 to each other in order to imitate the geometry of a spinal disc to be replaced by the present invention. As such, the plate body 20 of the first end plate 1, the plate body 20 of the second end plate 2, the inner core 3 and the outer core 4 may be understood to extend in a longitudinal direction between a proximal end 8 and a distal end 9. The proximal end 8 and the distal end 9 are positioned diametrically opposite each other for each of the plate body 20, the inner core 3, and the outer core 4. The proximal ends 8 are defined herein to be radially aligned with each other and the distal ends 9 are radially aligned with each other for each of the plate bodies of the first end plate 1 and the second end plate 2, the inner core 3, and the outer core 4. Thus, in some embodiments, the specified tilt angle 6 is defined in a plane coincident with the proximal ends 8 and the distal ends 9. In some embodiments comprising the flange attachment, the flange attachment is positioned at the proximal end 8 for each of the first end plate 1 and the second end plate 2. In various embodiments, the orientation and alignment of the specified tilt angle 6 may vary however, and should not be considered to be limited to the foregoing description.

Moreover, referring to FIGS. 7-8, in some embodiments, the specified tilt angle 6 may be realized through a diametrical difference in thickness of the inner core 3 and the outer core 4, so that the axial outer ends of the inner core 3 and outer core 4 are oriented at the specified tilt angle 6 to each other, and thus the first end plate 1 and the second end plate 2, being generally flat, are oriented at the specified tilt angle 6 to each other as a result. As such, a proximal thickness 10 and a distal thickness 11 of both the inner core 3 and the outer core 4 may be defined, wherein the proximal thickness 10 of the outer core 4 is the thickness of the outer core 4 at the proximal end 8 of the outer core 4, the distal thickness 11 of the outer core 4 is the thickness of the outer core 4 at the distal end 9 of the outer core 4, the proximal thickness 10 of the inner core 3 is the thickness of the inner core 3 at the proximal end 8 of the inner core 3, and the distal thickness 11 of the inner core 3 is the thickness of the inner core 3 at the distal end 9 of the inner core 3.

Thus, in some embodiments, the proximal thickness 10 of the inner core 3 is greater than the distal thickness 11 of the inner core 3, and the proximal thickness 10 of the outer core 4 is greater than the distal thickness 11 of the outer core 4. Thus, the specified tilt angle 6 may be determined in some embodiments by the difference between the proximal thicknesses 10 and the distal thicknesses 11. In other embodiments, the specified tilt angle 6 may be determined through other means; for example, the thickness of the inner core 3 and outer core 4 may be constant, while the thickness of the first end plate 1 and second end plate 2 may vary instead.

In some embodiments of the present invention, as shown in FIG. 9, as an alternative to the attachment flange 25, the first end plate 1 and the second end plate 2 further comprise a plurality of anchoring protrusions 12. The plurality of anchoring protrusions 12 serve as an alternative means of mounting the first end plate 1 and the second end plate 2 to adjacent vertebrae. The anchoring protrusions 12 are connected to the outer side 22 and are preferably oriented perpendicular to the plate body 20. The anchoring protrusions 12 are distributed around the outer side 22 in any desirable configuration, such as, but not limited to, four anchoring protrusions positioned in a concentric 90 degree pattern around the plate convexity 25. Furthermore, each of the anchoring protrusions 12 may comprise a plurality of teeth 13 positioned at a distal end 14 of the anchoring protrusions 12.

The components of the present invention may be manufactured through any desirable manufacturing process, such as, but not limited to, 3D printing, CNC machining, injection molding, compression bolding, or other manufacturing processes. The inner core 3 is preferably injection molded through an insert molding process where the first end plate 1 and the second end plate 2 serve as inserts. Alternatively, the inner core 3 can be produced independently through an injection molding, compression molding, or 3D printing process and is subsequently assembled with the first end plate 1 and the second end plate 2. The outer core 4 is preferably either injection molded or compression molded using an insert molding process where an assembly of the first end plate 1, second end plate 2, and inner core 3 serve as inserts. Alternatively, the outer core 4 can be produced independently through injection molding, compression molding, or 3D printing and subsequently assembled with the first end plate 1, second end plate 2, and inner core 3. Furthermore, in the preferred embodiment, at every stage of assembly of the present invention, the external surfaces of the various components of the present invention are treated to increase surface bonding to achieve sufficient covalent, cohesive and/or adhesive bonds.

FIGS. 12-15 show a second alternate embodiment of the present invention wherein the inner cavity 40 of the outer core 4 is positioned offset from concentric with the outer core centerline 17, and the first core convexity 30 and second core convexity 31 of the inner core 3 are positioned offset from concentric with the inner core centerline 16. Furthermore, the inner core centerline 16 and the outer core centerline 17 are also offset from each other. This geometric arrangement may have various advantages in different use cases, such as facilitating conformity to a patient's vertebrae. The second alternate embodiment additionally utilizes the previously discussed adhesive to bond the outer core 4 to the first end plate 1 and the second end plate 2.

FIGS. 16-19 show a third alternate embodiment, wherein the peripheral geometry of the inner core 3 and outer core 4 are generally rectilinear. This geometric arrangement may also have similar various advantages in different use cases or implantation scenarios, such as facilitating ease of insertion of the present invention between vertebrae.

FIGS. 20-24 show a fourth alternate embodiment, wherein the peripheral geometry of the inner core 3 and outer core 4 are generally rectilinear, as with the third alternate embodiment, while the outer core 4 is connected between the first end plate 1 and the second end plate 2 through the adhesive, as with the second alternate embodiment. Different embodiments comprising various combinations of the aforementioned features may be considered to be more or less advantageous in various situations, and the present invention should not be considered to be strictly limited to any of the specifically described embodiments herein.

Although the invention has been explained in relation to its preferred embodiment, it is to be understood that many other possible modifications and variations can be made without departing from the spirit and scope of the invention as hereinafter claimed.

What is claimed is:

1. A motion preserving spinal implant for total disc replacement comprising:
    a first end plate;
    a second end plate;
    an inner core;
    an outer core;
    the first end plate and the second end plate each comprising a plate body, an inner side, an outer side, a plate convexity, and a concavity, wherein a thickness of the plate body extends between the inner side and the outer side;
    the inner core comprising a first core convexity and a second core convexity positioned opposite each other along a thickness of the inner core;
    the outer core being connected between the first end plate and the second end plate;
    the outer core comprising an inner cavity;
    the inner cavity centrally traversing through the outer core;
    the inner core being positioned within the inner cavity of the outer core, wherein the inner core is sealed by the outer core, the first end plate and the second end plate;
    the plate body of the first end plate and the plate body of the second end plate being oriented at a specified tilt angle to each other, wherein the specified tilt angle defines a deviation of the plate body of the first end plate and the plate body of the second end plate from being oriented parallel to each other;
    the plate convexity being centrally positioned on the outer side of the plate body for each of the first end plate and the second end plate;
    the concavity being centrally positioned on the inner side of the plate body for each of the first end plate and the second end plate;
    the first core convexity being positioned within the concavity of the first end plate;
    the second core convexity being positioned within the concavity of the second end plate;
    the outer core being connected between the first end plate and the second end plate through a plurality of interlocking members;
    the inner side of the first end plate being connected to the outer core through the plurality of interlocking members;
    the inner side of the second end plate being connected to the outer core through the plurality of interlocking members opposite the first end plate along the thickness of the inner core.

2. The motion preserving spinal implant for total disc replacement as claimed in claim 1 comprising:
    the inner cavity centrally and axially traversing through the outer core; and
    the inner core being positioned concentrically within the inner cavity.

3. The motion preserving spinal implant for total disc replacement as claimed in claim 1, wherein the first end plate, the second end plate, the inner core, and the outer core each have rectilinear peripheral geometry.

4. The motion preserving spinal implant for total disc replacement as claimed in claim 1 comprising:
    the inner core and the outer core each comprising a radial axis and a central axis;
    the radial axis being positioned offset from the central axis for each of the inner core and the outer core; and
    the first core convexity and the second core convexity of the inner core being concentrically positioned about the radial axis of the inner core.

5. The motion preserving spinal implant for total disc replacement as claimed in claim 1, wherein the outer core is connected between the first end plate and the second end plate through an adhesive.

6. The motion preserving spinal implant for total disc replacement as claimed in claim 1, wherein the specified tilt angle is within a range of 0 to 15 degrees.

7. The motion preserving spinal implant for total disc replacement as claimed in claim 1, wherein the inner core is constructed of a polymeric material.

8. The motion preserving spinal implant for total disc replacement as claimed in claim 1, wherein the first end plate and the second end plate are constructed of a polyether ether ketone (PEEK) material.

9. The motion preserving spinal implant for total disc replacement as claimed in claim 1, wherein the inner core is constructed of a liquid silicon rubber with varying hardness.

10. The motion preserving spinal implant for total disc replacement as claimed in claim 1, wherein the outer core is constructed of a liquid silicon rubber with varying hardness.

11. The motion preserving spinal implant for total disc replacement as claimed in claim 1, wherein the outer core is constructed of a polymeric material.

12. The motion preserving spinal implant for total disc replacement as claimed in claim 1 comprising:
    the first end plate and the second end plate each further comprising an attachment flange and at least one fastener aperture;

the attachment flange being perpendicularly and perimetrically connected to the plate body and extending away from the inner side, past the outer side for each of the first end plate and the second end plate, wherein the attachment flange is connected along a flange arc segment of the perimeter of the plate body; and the at least one fastener aperture traversing through the attachment flange for each of the first end plate and the second end plate.

13. The motion preserving spinal implant for total disc replacement as claimed in claim 12 comprising:

the attachment flange comprising an inner groove; and the inner groove traversing radially through the attachment flange along the flange arc segment adjacent to the outer side and adjacent to a perimeter of the plate body for each of the first end plate and the second end plate.

14. The motion preserving spinal implant for total disc replacement as claimed in claim 1 comprising:

the outer core comprising a first plurality of core interlocking members and a second plurality of core interlocking members from the plurality of interlocking members, wherein the first plurality of core interlocking members and the second plurality of core interlocking members are positioned opposite each other along a thickness of the outer core;

the first end plate and the second end plate each further comprising a plurality of plate interlocking members from the plurality of interlocking members;

the plurality of plate interlocking members being positioned concentrically around the concavity on the inner side of the plate body for each of the first end plate and the second end plate;

the first plurality of core interlocking members of the outer core being engaged with the plurality of plate interlocking members of the first end plate; and the second plurality of core interlocking members of the outer core being engaged with the plurality of plate interlocking members of the second end plate.

15. The motion preserving spinal implant for total disc replacement as claimed in claim 14 comprising:

a plurality of interlocking member receiving channels;

each of the plurality of interlocking member receiving channels being positioned concentrically with and adjacent to one of the plurality of interlocking members; and each of the plurality of interlocking members being positioned within one of the plurality of interlocking member receiving channels, wherein the plurality of interlocking members and the plurality of interlocking member receiving channels are configured to resist extrusion of the inner core and outer core when the inner core and outer core are subject to external forces.

16. The motion preserving spinal implant for total disc replacement as claimed in claim 1 comprising:

the plate body of the first end plate, the plate body of the second end plate, the inner core and the outer core each extending longitudinally between a proximal end and a distal end, wherein the proximal end and the distal end are positioned diametrically opposite each other for each of the plate body, the inner core, and the outer core, wherein the proximal ends are radially aligned with each other and the distal ends are radially aligned with each other for each of the plate bodies of the first end plate and second end plate, the inner core, and the outer core, and wherein the specified tilt angle is defined in a plane coincident with the proximal ends and the distal ends.

17. The motion preserving spinal implant for total disc replacement as claimed in claim 16 comprising:

the first end plate and the second end plate each further comprising a flange attachment; and the flange attachment being positioned at the proximal end for each of the first end plate and the second end plate.

18. The motion preserving spinal implant for total disc replacement as claimed in claim 16 comprising:

a proximal thickness of the inner core at the proximal end of the inner core being greater than a distal thickness of the inner core at the distal end of the inner core; and a proximal thickness of the outer core at the proximal end of the outer core being greater than a distal thickness of the outer core at the distal end of the outer core, wherein the specified tilt angle is determined by the difference between the proximal thicknesses and the distal thicknesses.

* * * * *